United States Patent [19]

Takano et al.

[11] Patent Number: 5,714,437
[45] Date of Patent: Feb. 3, 1998

[54] EPOXYPHENOL DERIVATIVES AND HERBICIDES CONTAINING THEM AS ACTIVE INGREDIENTS

[75] Inventors: Minoru Takano, Kameoka; Masayuki Enomoto, Takarazuka; Kazuo Saito, Funabashi; Satoru Kizawa, Kakogawa, all of Japan

[73] Assignee: Sumitomo Chemical Company, Limited, Osaka-fu, Japan

[21] Appl. No.: 520,872

[22] Filed: Aug. 30, 1995

[30] Foreign Application Priority Data

Aug. 31, 1994 [JP] Japan ............... 6-206834

[51] Int. Cl.$^6$ ............... C07D 405/10; C07D 413/10; C07D 417/10; A61K 31/505
[52] U.S. Cl. ............... 504/238; 504/243; 544/237; 544/314; 544/311; 544/313; 544/91; 544/55; 544/235; 548/465; 548/262.4; 548/302.7; 548/144; 548/145; 548/363.1; 548/226; 548/126; 548/184; 548/193; 546/114
[58] Field of Search ............... 544/314, 311, 544/313, 237; 504/243, 238

[56] References Cited

U.S. PATENT DOCUMENTS

| | | | |
|---|---|---|---|
| 4,326,879 | 4/1982 | Spencer et al. | 71/94 |
| 4,468,245 | 8/1984 | Takematsu et al. | 71/88 |
| 4,859,230 | 8/1989 | Blume et al. | 71/93 |
| 4,881,967 | 11/1989 | Semple | 71/92 |
| 4,941,909 | 7/1990 | Wenger et al. | 71/92 |
| 5,006,148 | 4/1991 | Fischer et al. | 71/72 |
| 5,041,156 | 8/1991 | Suchy et al. | 71/92 |
| 5,411,935 | 5/1995 | Takemura et al. | 504/243 |
| 5,476,834 | 12/1995 | Takemura et al. | 504/243 |

FOREIGN PATENT DOCUMENTS

| | | |
|---|---|---|
| 0075267 | 3/1983 | European Pat. Off. . |
| 0170191 | 2/1986 | European Pat. Off. . |
| 0208374 | 1/1987 | European Pat. Off. . |
| 0268797 | 6/1988 | European Pat. Off. . |
| 0271170 | 6/1988 | European Pat. Off. . |
| 0370332 | 5/1990 | European Pat. Off. . |
| 0493606 | 7/1992 | European Pat. Off. . |
| 0517181 | 12/1992 | European Pat. Off. . |
| 0617033 | 9/1994 | European Pat. Off. . |
| 60-233075 | 11/1985 | Japan . |

OTHER PUBLICATIONS

Ohta et al.; "Quantitative Structure–Activity Study of Herbicidal N–Aryl–3,4,5,6–tetrahydrophthalimides and Related Cyclic Imides"; *Pesticide Biochemistry and Physiology* 14, 153–160 (1980), pp. 153–160.

*Primary Examiner*—Mukund J. Shah
*Assistant Examiner*—King Lit Wong
*Attorney, Agent, or Firm*—Birch, Stewart, Kolasch & Birch, LLP

[57] ABSTRACT

Novel compounds of the formula [1] are disclosed, wherein X is hydrogen, fluorine or chlorine; Y is fluorine, chlorine or bromine; $R^1$ is hydrogen or $C_1$–$C_3$ alkyl; and $R^2$ and Q are various groups. Also disclosed are herbicidal compositions containing these compounds as active ingredients and methods for controlling unfavorable weeds by application of these compounds.

11 Claims, No Drawings

EPOXYPHENOL DERIVATIVES AND HERBICIDES CONTAINING THEM AS ACTIVE INGREDIENTS

FIELD OF THE INVENTION

The present invention relates to novel epoxyphenol derivatives and herbicides containing them as active ingredients.

SUMMARY OF THE INVENTION

The present inventors have intensively studied to develop excellent herbicides and found that epoxyphenol derivatives represented by the formula [1] below have excellent herbicidal activity, thereby completing the present invention.

That is, the present invention provides novel compounds of the formula:

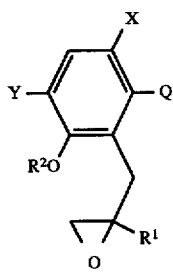

[1]

(hereinafter referred to as the present compound(s)) wherein:

X is hydrogen, fluorine or chlorine;
Y is fluorine, chlorine or bromine;
$R^1$ is hydrogen or $C_1$–$C_3$ alkyl;
$R^2$ is $C_1$–$C_6$ alkyl, $C_1$–$C_6$ haloalkyl, $C_1$–$C_6$ alkoxy ($C_1$–$C_6$) alkyl, $C_1$–$C_6$ alkoxy ($C_1$–$C_6$) alkoxy ($C_1$–$C_6$) alkyl, $C_1$–$C_6$ alkylthio ($C_1$–$C_6$) alkyl, $C_3$–$C_6$ alkenyl, $C_3$–$C_6$ haloalkenyl, $C_3$–$C_6$ alkynyl, $C_3$–$C_6$ haloalkynyl or $C_3$–$C_6$ cycloalkyl; or $R^2$ is a group of the formula:

—COR³ wherein $R^3$ is $C_1$–$C_6$ alkyl, $C_1$–$C_6$ haloalkyl, phenyl which may be optionally substituted with at least one halogen atom, $C_1$–$C_3$ alkyl group or $C_1$–$C_3$ alkoxy group; or a group of the formula:

—NR⁴R⁵ wherein $R^4$ and $R^5$ are independently hydrogen, $C_1$–$C_6$ alkyl or $C_1$–$C_6$ haloalkyl; or $R^2$ is a group of the formula:

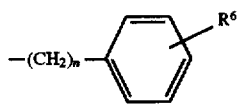

wherein n is an integer of 1 to 5; $R^6$ is hydrogen, halogen, $C_1$–$C_3$ alkyl or $C_1$–$C_3$ alkoxy; or $R^2$ is a group of the formula:

—CR⁷R⁸COOR⁹ wherein $R^7$ and $R^8$ are independently hydrogen or $C_1$–$C_3$ alkyl; $R^9$ is hydrogen, $C_1$–$C_6$ alkyl, $C_1$–$C_6$ haloalkyl or $C_3$–$C_6$ cycloalkyl; or $R^2$ is a group of the formula:

—SO₂R¹⁰ wherein $R^{10}$ is $C_1$–$C_6$ alkyl or $C_1$–$C_6$ haloalkyl; or phenyl which may be optionally substituted with at least one $C_1$–$C_3$ alkyl group; and —Q is one of the groups Q-1 to Q-13 of the following formulae:

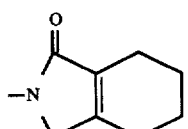

Q-1

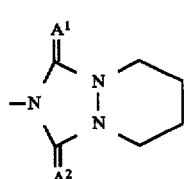

Q-2

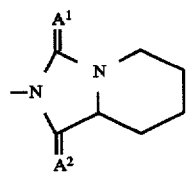

Q-3

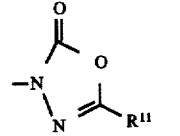

Q-4

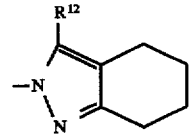

Q-5

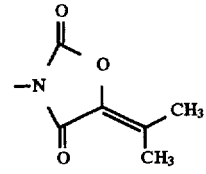

Q-6

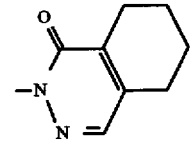

Q-7

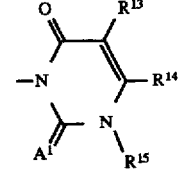

Q-8

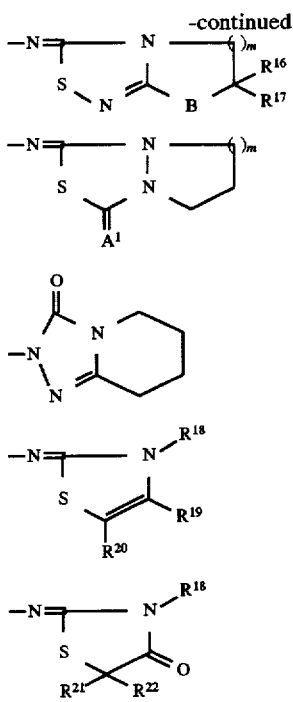

wherein $A^1$ and $A^2$ are independently oxygen or sulfur;

B is oxygen, sulfur or methylene;

$R^{11}$ is $C_1-C_6$ alkyl which may be optionally substituted with at least one halogen atom; or $C_3-C_6$ cycloalkyl which may be optionally substituted with at least one $C_1-C_3$ alkyl group;

$R^{12}$ is chlorine, methyl or $C_1-C_3$ alkoxy;

$R^{13}$ is hydrogen, halogen or $C_1-C_3$ alkyl;

$R^{14}$ is $C_1-C_3$ alkyl which may be substituted with at least one halogen atom;

$R^{15}$ is hydrogen, $C_1-C_6$ alkyl, $C_3-C_6$ alkenyl, $C_3-C_6$ alkynyl, amino or benzyl;

$R^{16}$ and $R^{17}$ are independently hydrogen or $C_1-C_3$ alkyl;

$R^{18}$ is $C_1-C_6$ alkyl which may be optionally substituted with at least one halogen atom; $C_3-C_6$ alkynyl which may be optionally substituted with at least one halogen atom; or $C_3-C_6$ alkenyl which may be optionally substituted with at least one halogen atom;

$R^{19}$ is hydrogen or $C_1-C_6$ alkyl which may be optionally substituted with at least one halogen atom; or $C_7-C_{17}$ aralkyl or aryl;

$R^{20}$ is hydrogen or $C_1-C_6$ alkyl which may be optionally substituted with at least one halogen atom;

$R^{21}$ and $R^{22}$ are independently hydrogen or halogen; or $C_1-C_6$ alkyl which may be optionally substituted with at least one halogen atom; and m is an integer of 1 or 2.

The present invention further provides herbicides containing the above compounds as active ingredients.

Some of the present compounds have optical isomers based on the presence of at least one asymmetrical carbon atom, and these optical isomers are, of course, included within the scope of the present invention.

In the above definition of the present compounds, the respective substituents are exemplified as follows:

Examples of the $C_1-C_3$ alkyl represented by $R^1$ include methyl.

Examples of the $C_1-C_6$ alkyl represented by $R^2$ include methyl, ethyl, isopropyl, sec-butyl and t-butyl.

Examples of the $C_1-C_6$ haloalkyl represented by $R^2$ include difluoromethyl and tetrafluoroethyl.

Examples of the $C_1-C_6$ alkoxy ($C_1-C_6$) alkyl represented by $R^2$ include methoxymethyl, ethoxymethyl and methoxyethyl.

Examples of the $C_1-C_6$ alkoxy ($C_1-C_6$) alkoxy ($C_1-C_6$) alkyl represented by $R^2$ include methoxyethoxymethyl.

Examples of the $C_1-C_6$ alkylthio ($C_1-C_6$) alkyl represented by $R^2$ include methylthiomethyl.

Examples of the $C_3-C_6$ alkenyl represented by $R^2$ include allyl, 1-methyl-2-propenyl, 3-butenyl, 2-butenyl, 3-methyl-2-butenyl and 2-methyl-3-butenyl.

Examples of the $C_3-C_6$ haloalkenyl represented by $R^2$ include 2-chloro-2-propenyl and 3,3-dichloro-2-propenyl.

Examples of the $C_3-C_6$ alkynyl represented by $R^2$ include propargyl, 1-methyl-2-propynyl, 2-butynyl and 1,1-dimethyl-2-propynyl.

Examples of the $C_3-C_6$ haloalkynyl represented by $R^2$ include 3-iodo-2-propynyl and 3-bromo-2-propynyl.

Examples of the $C_3-C_6$ cycloalkyl represented by $R^2$ include cyclopropyl, cyclopentyl and cyclohexyl.

Examples of the group of the formula: —$COR^3$, which is represented by $R^2$, include acetyl, propanoyl, trifluoroacetyl, chloroacetyl, 2-methylpropanoyl, dichloroacetyl, pivaloyl, benzoyl, 4-methoxybenzoyl and dimethylaminocarbonyl.

Examples of the group of the formula:

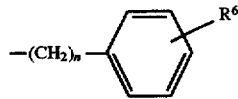

which is represented by $R^2$, include benzyl and phenetyl.

Examples of the group of the formula: —$CR^7R^8COOR^9$, which is represented by $R^2$, include methoxycarbonylmethyl, ethoxycarbonylmethyl, n-amyloxycarbonylmethyl, isopropoxycarbonylmethyl, 1-methoxycarbonylethyl, cyclopentyloxycarbonylmethyl and cyclohexyloxycarbonylmethyl.

Examples of the group of the formula: —$SO_2R^{10}$, which is represented by $R^2$, include methanesulfonyl, ethanesulfonyl, chloromethanesulfonyl, benzenesulfonyl and 4-toluenesulfonyl.

Examples of the $C_1-C_6$ alkyl optionally substituted with at least one halogen atom, which is represented by $R^{11}$, include methyl, isopropyl and tert-butyl.

Examples of the $C_3-C_6$ cycloalkyl optionally substituted with at least one $C_1-C_3$ alkyl group, which is represented by $R^{11}$, include 1-methylcyclopropyl.

Examples of the $C_1-C_3$ alkoxy represented by $R^{12}$ include methoxy.

Examples of the halogen represented by $R^{13}$ include chlorine.

Examples of the $C_1-C_3$ alkyl represented by $R^{13}$ include methyl.

Examples of the $C_1-C_3$ alkyl optionally substituted with at least one halogen atom, which is represented by $R^{14}$, include trifluoromethyl and pentafluoroethyl.

Examples of the $C_1-C_6$ alkyl represented by $R^{15}$ include methyl.

Examples of the $C_3-C_6$ alkenyl represented by $R^{15}$ include allyl.

Examples of the $C_3-C_6$ alkynyl represented by $R^{15}$ include propargyl.

Examples of the $C_1-C_3$ alkyl represented by $R^{16}$ and $R^{17}$ include methyl.

Examples of the $C_1-C_6$ alkyl optionally substituted with at least one halogen atom, which is represented by $R^{18}$, include methyl.

Examples of the $C_3-C_6$ alkynyl optionally substituted with at least one halogen atom, which is represented by $R^{18}$, include propargyl.

Examples of the $C_3-C_6$ alkenyl optionally substituted with at least one halogen atom, which is represented by $R^{18}$, include allyl.

Examples of the $C_1-C_6$ alkyl optionally substituted with at least one halogen atom, which is represented by $R^{19}$, include methyl and trifluoromethyl.

Examples of the $C_7-C_{17}$ aralkyl represented by $R^{19}$ include benzyl.

Examples of the aryl represented by $R^{19}$ include phenyl.

Examples of the $C_1-C_6$ alkyl optionally substituted with at least one halogen atom, which is represented by $R^{20}$, include methyl.

Examples of the halogen represented by $R^{21}$ and $R^{22}$ include chlorine.

Examples of the $C_1-C_6$ alkyl optionally substituted with at least one halogen atom, which is represented by $R^{21}$ and $R^{22}$, include methyl.

From the viewpoint of herbicidal activity, preferred substituents represented by $R^1$ are hydrogen and methyl, and preferred substituents represented by $R^2$ are acetyl, benzoyl, methylthiomethyl and methoxymethyl.

Preferred compounds are those wherein X is fluorine, Y is chlorine, $R^1$ is methyl, $R^2$ is acetyl or methylthiomethyl,—Q is a group of the formula Q-8, $A^1$ is oxygen, $R^{13}$ is hydrogen, $R^{14}$ is trifluoromethyl, and $R^{15}$ is methyl.

The present compounds can be produced by, for example, a process comprising reacting an allylphenol derivative of the formula:

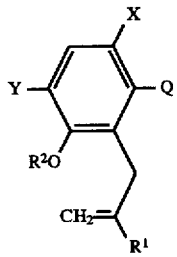

[2]

wherein X, Y, Q, $R^1$ and $R^2$ are each as defined above, with an epoxidizing agent.

The reaction is usually effected in a solvent. The reaction temperature is usually in the range of −20° to 150° C., preferably 0° to 50° C. The reaction time is usually in the range of a moment to 48 hours. The amount of the epoxidizing agent to be used in the reaction is usually 1 to 5 moles per mole of the compound [2].

Examples of the solvent which can be used include aliphatic hydrocarbons such as petroleum ether and hexane; fatty acids such as formic acid and acetic acid; and halogenated hydrocarbons such as methylene chloride, chloroform and 1,2-dichloroethane. Examples of the epoxidizing agent include peracids such as perbenzoic acid, m-chloroperbenzoic acid, peracetic acid and trifluoroperacetic acid; and mixtures thereof.

After completion of the reaction, the reaction mixture is treated, if necessary, with a reducing agent such as aqueous sodium thiosulfate solution or aqueous sodium hydrogensulfite solution to remove excess epoxidizing agent, followed by ordinary post-treatments such as extraction with an organic solvent and concentration, and if necessary, subsequent purification such as chromatography or recrystallization. Thus, the present compounds can be isolated.

Some of the present compounds can be produced by introducing an $R^2$ moiety into a phenol derivative of the formula:

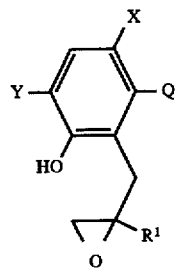

[3]

wherein X, Y, Q and $R^1$ are each as defined above. The method for introducing the $R^2$ moiety includes the following methods (a), (b) and (c), which are selected depending upon the $R^2$.

(a) The present compounds wherein $R^2$ is $C_1-C_6$ alkoxymethyl or $C_1-C_6$ alkoxy ($C_1-C_6$) alkoxymethyl can be produced by reacting the compound [3] with a compound of the formula:

$$R^{21}-L \qquad [4]$$

wherein $R^{21}$ is $C_1-C_6$ alkoxymethyl or $C_1-C_6$ alkoxy ($C_1-C_6$) alkoxymethyl; and L is chlorine, bromine or iodine, methanesulfonyloxy or p-toluenesulfonyloxy.

The reaction is usually effected in a solvent in the presence of a base. The reaction temperature is usually in the range of <20° to 100° C. or the refluxing temperature of the solvent. The reaction time is usually in the range of a moment to 48 hours. The amounts of the reagents to be used in the reaction are usually 1 to 5 moles of the compound [4] and usually 1 mole to an excess of the base, per mole of the compound [3].

Examples of the solvent which can be used include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; acid amides such as N,N-dimethylformamide and acetamide; tertiary amines such as pyridine, triethylamine, N,N-dimethylaniline, N,N-diethylaniline and N-methylmorpholine; sulfur compounds such as dimethylsulfoxide and sulfolane; and mixtures thereof.

Examples of the base which can be used include organic bases such as triethylamine, diisopropylethylamine, pyridine, 4-dimethylaminopyridine and N,N-dimethylaniline; and mixtures thereof.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification such as chromatography or recrystallization. Thus, the present compounds can be isolated.

(b) The present compounds wherein $R^2$ is a group of the formula: —$COR^3$ can be produced by reacting the compound [3] with a compound of the formula:

$$R^3CO-G \qquad [5]$$

wherein $R^3$ is as defined above and G is chlorine or bromine, or with a compound of the formula:

$$(R^3CO)_2O \quad [6]$$

wherein $R^3$ is as defined above.

The reaction is usually effected without any solvent or in a solvent in the presence of a base. The reaction temperature is usually in the range of <20° to 200° C., preferably 0° C. to the refluxing temperature of the solvent when used, or preferably 0° to 100° C. in the absence of solvents. The reaction time is usually in the range of a moment to 24 hours. The amounts of the reagents to be used in the reaction are usually 1 mole to a large excess of the compound [5] or [6] and usually 1 mole to a large excess of the base, per mole of the compound [3].

Examples of the solvent which can be used include aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; sulfur compounds such as dimethylsulfoxide and sulfolane; and mixtures thereof.

Examples of the base which can be used include organic bases such as triethylamine, diisopropylethylamine, pyridine, 4-dimethylaminopyridine and N,N-dimethylaniline; and mixtures thereof.

After completion of the reaction, the reaction mixture is concentrated or poured into water, and the precipitated crystals are collected by filtration, or the reaction mixture is subjected to ordinary post-treatments such as extraction with an organic solvent and concentration, followed by, if necessary, subsequent purification such as chromatography or recrystallization. Thus, the present compounds can be isolated.

(c) The present compounds wherein $R^2$ is methylthiomethyl can be produced by reacting the compound [3] with acetic anhydride and dimethylsulfoxide.

The reaction is usually effected without any solvent or in a solvent. The reaction temperature is usually in the range of 0° to 100° C. The reaction time is usually in the range of a moment to 24 hours. The mounts of the reagents to be used in the reaction are usually 1 mole to a large excess of acetic anhydride and usually 1 mole to a large excess of dimethylsulfoxide, per mole of the compound [3].

Examples of the solvent which can be used include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; acid amides such as formamide, N,N-dimethylformamide and acetamide; sulfur compounds such as dimethylsulfoxide and sulfolane; and mixtures thereof.

After completion of the reaction, the reaction mixture is poured into water, and the precipitated crystals are collected by filtration, or the reaction mixture is concentrated or subjected to ordinary post-treatments such as extraction with an organic solvent and concentration, followed by, if necessary, subsequent purification such as chromatography or recrystallization. Thus, the present compounds can be isolated.

Examples of the present compounds are shown in Tables 1 to 13 below; however, the present compounds are not limited to these examples. In Tables 1 to 13, "c $C_5H_9$", "c $C_6H_{11}$", ""$C_4H_9$", ""$C_5H_{11}$", "p-$CH_3OC_6H_4$", "p-$CH_3C_6H_4$" and "p-$ClC_6H_4$" mean cyclopentyl, cyclohexyl, normal butyl, normal pentyl, p-methoxyphenyl, p-methylphenyl and p-chlorophenyl, respectively.

TABLE 1

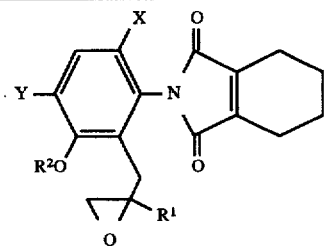

(compound wherein Q is Q-1.)

| Compound No. | X | Y | $R^1$ | $R^2$ |
|---|---|---|---|---|
| 1-1 | F | Cl | H | $CH_3$ |
| 1-2 | F | Cl | H | $C_2H_5$ |
| 1-3 | F | Cl | H | $(CH_3)_2CH$ |
| 1-4 | F | Cl | H | $(CH_3)_3C$ |
| 1-5 | F | Cl | H | $ClCH_2CH_2$ |
| 1-6 | F | Cl | H | $CH_3OCH_2$ |
| 1-7 | F | Cl | H | $C_2H_5OCH_2$ |
| 1-8 | F | Cl | H | $CH_3OCH_2CH_2$ |
| 1-9 | F | Cl | H | $CH_3OCH_2CH_2OCH_2$ |
| 1-10 | F | Cl | H | $CH_3SCH_2$ |
| 1-11 | F | Cl | H | $CH_2=CHCH_2$ |
| 1-12 | F | Cl | H | $CH_2=CHCH_2CH_2$ |
| 1-13 | F | Cl | H | $CH_3-CH=CHCH_2$ |
| 1-14 | F | Cl | H | $CH_2=CClCH_2$ |
| 1-15 | F | Cl | H | $CCl_2=CHCH_2$ |
| 1-16 | F | Cl | H | $CH\equiv CCH_2$ |
| 1-17 | F | Cl | H | $CH\equiv CCH(CH_3)$ |
| 1-18 | F | Cl | H | $BrC\equiv CCH_2$ |
| 1-19 | F | Cl | H | $cC_5H_9$ |
| 1-20 | F | Cl | H | $cC_6H_{11}$ |
| 1-21 | F | Cl | H | $CH_3CO$ |
| 1-22 | F | Cl | H | $C_2H_5CO$ |
| 1-23 | F | Cl | H | $(CH_3)_2CHCO$ |
| 1-24 | F | Cl | H | $(CH_3)_3CCO$ |
| 1-25 | F | Cl | H | $C_6H_5CO$ |
| 1-26 | F | Cl | H | p-$CH_3OC_6H_4CO$ |
| 1-27 | F | Cl | H | p-$CH_3C_6H_4CO$ |
| 1-28 | F | Cl | H | $ClCH_2CO$ |
| 1-29 | F | Cl | H | $CH_3NHCO$ |
| 1-30 | F | Cl | H | $(CH_3)_2NCO$ |
| 1-31 | F | Cl | H | $(C_2H_5)_2NCO$ |
| 1-32 | F | Cl | H | $C_6H_5CH_2$ |
| 1-33 | F | Cl | H | p-$CH_3OC_6H_4CH_2$ |
| 1-34 | F | Cl | H | p-$ClC_6H_4CH_2$ |
| 1-35 | F | Cl | H | $C_6H_5CH_2CH_2$ |
| 1-36 | F | Cl | H | $CH_3OOCCH_2$ |
| 1-37 | F | Cl | H | $C_2H_5OOCCH_2$ |
| 1-38 | F | Cl | H | $(CH_3)_2CHOOCCH_2$ |
| 1-39 | F | Cl | H | $^nC_4H_9OOCCH_2$ |
| 1-40 | F | Cl | H | $^nC_5H_{11}OOCCH_2$ |

TABLE 1-continued

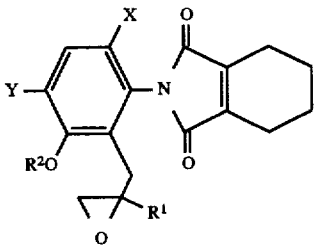

(compound wherein Q is Q-1.)

| Compound No. | X | Y | R¹ | R² |
|---|---|---|---|---|
| 1-41 | F | Cl | H | CH$_3$OOCCH(CH$_3$) |
| 1-42 | F | Cl | H | C$_2$H$_5$OOCCH(CH$_3$) |
| 1-43 | F | Cl | H | cC$_5$H$_9$OOCCH$_2$ |
| 1-44 | F | Cl | H | cC$_6$H$_{11}$OOCCH$_2$ |
| 1-45 | F | Cl | H | CH$_3$SO$_2$ |
| 1-46 | F | Cl | H | C$_2$H$_5$SO$_2$ |
| 1-47 | F | Cl | H | (CH$_3$)$_2$CHSO$_2$ |
| 1-48 | F | Cl | H | ClCH$_2$SO$_2$ |
| 1-49 | F | Cl | H | C$_6$H$_5$SO$_2$ |
| 1-50 | F | Cl | H | p-CH$_3$C$_6$H$_4$SO$_2$ |
| 1-51 | F | Cl | CH$_3$ | CH$_3$ |
| 1-52 | F | Cl | CH$_3$ | C$_2$H$_5$ |
| 1-53 | F | Cl | CH$_3$ | (CH$_3$)$_2$CH |
| 1-54 | F | Cl | CH$_3$ | (CH$_3$)$_3$C |
| 1-55 | F | Cl | CH$_3$ | ClCH$_2$CH$_2$ |
| 1-56 | F | Cl | CH$_3$ | CH$_3$OCH$_2$ |
| 1-57 | F | Cl | CH$_3$ | C$_2$H$_5$OCH$_2$ |
| 1-58 | F | Cl | CH$_3$ | CH$_3$OCH$_2$CH$_2$ |
| 1-59 | F | Cl | CH$_3$ | CH$_3$OCH$_2$CH$_2$OCH$_2$ |
| 1-60 | F | Cl | CH$_3$ | CH$_3$SCH$_2$ |
| 1-61 | F | Cl | CH$_3$ | CH$_2$=CHCH$_2$ |
| 1-62 | F | Cl | CH$_3$ | CH$_2$=CHCH$_2$CH$_2$ |
| 1-63 | F | Cl | CH$_3$ | CH$_3$—CH=CHCH$_2$ |
| 1-64 | F | Cl | CH$_3$ | CH$_2$=CClCH$_2$ |
| 1-65 | F | Cl | CH$_3$ | CCl$_2$=CHCH$_2$ |
| 1-66 | F | Cl | CH$_3$ | CH≡CCH$_2$ |
| 1-67 | F | Cl | CH$_3$ | CH≡CC(CH$_3$) |
| 1-68 | F | Cl | CH$_3$ | BrC≡CHCH$_2$ |
| 1-69 | F | Cl | CH$_3$ | cC$_5$H$_9$ |
| 1-70 | F | Cl | CH$_3$ | cC$_6$H$_{11}$ |
| 1-71 | F | Cl | CH$_3$ | CH$_3$CO |
| 1-72 | F | Cl | CH$_3$ | C$_2$H$_5$CO |
| 1-73 | F | Cl | CH$_3$ | (CH$_3$)$_2$CHCO |
| 1-74 | F | Cl | CH$_3$ | (CH$_3$)$_3$CCO |
| 1-75 | F | Cl | CH$_3$ | C$_6$H$_5$CO |
| 1-76 | F | Cl | CH$_3$ | p-CH$_3$OC$_6$H$_4$CO |
| 1-77 | F | Cl | CH$_3$ | p-CH$_3$C$_6$H$_5$CO |
| 1-78 | F | Cl | CH$_3$ | ClCH$_2$CO |
| 1-79 | F | Cl | CH$_3$ | CH$_3$NHCO |
| 1-80 | F | Cl | CH$_3$ | (CH$_3$)$_2$NCO |
| 1-81 | F | Cl | CH$_3$ | (C$_2$H$_5$)$_2$NCO |
| 1-82 | F | Cl | CH$_3$ | C$_6$H$_5$CH$_2$ |
| 1-83 | F | Cl | CH$_3$ | p-CH$_3$OC$_6$H$_4$CH$_2$ |
| 1-84 | F | Cl | CH$_3$ | p-ClC$_6$H$_4$CH$_2$ |
| 1-85 | F | Cl | CH$_3$ | C$_6$H$_5$CH$_2$CH$_2$ |
| 1-86 | F | Cl | CH$_3$ | CH$_3$OOCCH$_2$ |
| 1-87 | F | Cl | CH$_3$ | C$_2$H$_5$OOCCH$_2$ |
| 1-88 | F | Cl | CH$_3$ | (CH$_3$)$_2$CHOOCCH$_2$ |
| 1-89 | F | Cl | CH$_3$ | ⁿC$_4$H$_9$OOCCH$_2$ |
| 1-90 | F | Cl | CH$_3$ | ⁿC$_5$H$_{11}$OOCCH$_2$ |
| 1-91 | F | Cl | CH$_3$ | CH$_3$OOCCH(CH$_3$) |
| 1-92 | F | Cl | CH$_3$ | C$_2$H$_5$OOCCH(CH$_3$) |
| 1-93 | F | Cl | CH$_3$ | cC$_5$H$_9$OOCCH$_2$ |
| 1-94 | F | Cl | CH$_3$ | cC$_6$H$_{11}$OOCCH$_2$ |
| 1-95 | F | Cl | CH$_3$ | CH$_3$SO$_2$ |
| 1-96 | F | Cl | CH$_3$ | C$_2$H$_5$SO$_2$ |
| 1-97 | F | Cl | CH$_3$ | (CH$_3$)$_2$CHSO$_2$ |
| 1-98 | F | Cl | CH$_3$ | ClCH$_2$SO$_2$ |
| 1-99 | F | Cl | CH$_3$ | C$_6$H$_5$SO$_2$ |

TABLE 1-continued

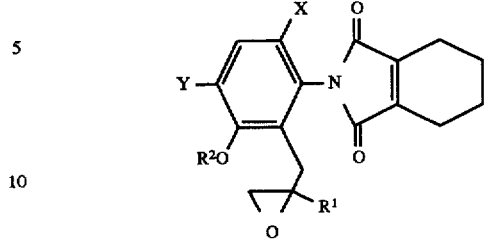

(compound wherein Q is Q-1.)

| Compound No. | X | Y | R¹ | R² |
|---|---|---|---|---|
| 1-100 | F | Cl | CH$_3$ | p-CH$_3$C$_6$H$_4$SO$_2$ |
| 1-101 | H | Cl | H | CH$_3$ |
| 1-102 | H | Cl | H | C$_2$H$_5$ |
| 1-103 | H | Cl | H | (CH$_3$)$_2$CH |
| 1-104 | H | Cl | H | (CH$_3$)$_3$C |
| 1-105 | H | Cl | H | ClCH$_2$CH$_2$ |
| 1-106 | H | Cl | H | CH$_3$OCH$_2$ |
| 1-107 | H | Cl | H | C$_2$H$_5$OCH$_2$ |
| 1-108 | H | Cl | H | CH$_3$OCH$_2$CH$_2$ |
| 1-109 | H | Cl | H | CH$_3$OCH$_2$CH$_2$OCH$_2$ |
| 1-110 | H | Cl | H | CH$_3$SCH$_2$ |
| 1-111 | H | Cl | H | CH$_2$=CHCH$_2$ |
| 1-112 | H | Cl | H | CH$_2$=CHCH$_2$CH$_2$ |
| 1-113 | H | Cl | H | CH$_3$—CH=CHCH$_2$ |
| 1-114 | H | Cl | H | CH$_2$=CClCH$_2$ |
| 1-115 | H | Cl | H | CCl$_2$=CHCH$_2$ |
| 1-116 | H | Cl | H | CH≡CCH$_2$ |
| 1-117 | H | Cl | H | CH≡CCH(CH$_3$) |
| 1-118 | H | Cl | H | BrC≡CCH$_2$ |
| 1-119 | H | Cl | H | cC$_5$H$_9$ |
| 1-120 | H | Cl | H | cC$_6$H$_{11}$ |
| 1-121 | H | Cl | H | CH$_3$CO |
| 1-122 | H | Cl | H | C$_2$H$_5$CO |
| 1-123 | H | Cl | H | (CH$_3$)$_2$CHCO |
| 1-124 | H | Cl | H | (CH$_3$)$_3$CCO |
| 1-125 | H | Cl | H | C$_6$H$_5$CO |
| 1-126 | H | Cl | H | p-CH$_3$OC$_6$H$_4$CO |
| 1-127 | H | Cl | H | p-CH$_3$C$_6$H$_5$CO |
| 1-128 | H | Cl | H | ClCH$_2$CO |
| 1-129 | H | Cl | H | CH$_3$NHCO |
| 1-130 | H | Cl | H | (CH$_3$)$_2$NCO |
| 1-131 | H | Cl | H | (C$_2$H$_5$)$_2$NCO |
| 1-132 | H | Cl | H | C$_6$H$_5$CH$_2$ |
| 1-133 | H | Cl | H | p-CH$_3$OC$_6$H$_4$CH$_2$ |
| 1-134 | H | Cl | H | p-ClC$_6$H$_4$CH$_2$ |
| 1-135 | H | Cl | H | C$_6$H$_5$CH$_2$CH$_2$ |
| 1-136 | H | Cl | H | CH$_3$OOCCH$_2$ |
| 1-137 | H | Cl | H | C$_2$H$_5$OOCCH$_2$ |
| 1-138 | H | Cl | H | (CH$_3$)$_2$CHOOCCH$_2$ |
| 1-139 | H | Cl | H | ⁿC$_4$H$_9$OOCCH$_2$ |
| 1-140 | H | Cl | H | ⁿC$_5$H$_{11}$OOCCH$_2$ |
| 1-141 | H | Cl | H | CH$_3$OOCCH(CH$_3$) |
| 1-142 | H | Cl | H | C$_2$H$_5$OOCCH(CH$_3$) |
| 1-143 | H | Cl | H | cC$_5$H$_9$OOCCH$_2$ |
| 1-144 | H | Cl | H | cC$_6$H$_{11}$OOCCH$_2$ |
| 1-145 | H | Cl | H | CH$_3$SO$_2$ |
| 1-146 | H | Cl | H | C$_2$H$_5$SO$_2$ |
| 1-147 | H | Cl | H | (CH$_3$)$_2$CHSO$_2$ |
| 1-148 | H | Cl | H | ClCH$_2$SO$_2$ |
| 1-149 | H | Cl | H | C$_6$H$_5$SO$_2$ |
| 1-150 | H | Cl | H | p-CH$_3$C$_6$H$_4$SO$_2$ |
| 1-151 | H | Cl | CH$_3$ | CH$_3$ |
| 1-152 | H | Cl | CH$_3$ | C$_2$H$_5$ |
| 1-153 | H | Cl | CH$_3$ | (CH$_3$)$_2$CH |
| 1-154 | H | Cl | CH$_3$ | (CH$_3$)$_3$C |
| 1-155 | H | Cl | CH$_3$ | ClCH$_2$CH$_2$ |
| 1-156 | H | Cl | CH$_3$ | CH$_3$OCH$_2$ |
| 1-157 | H | Cl | CH$_3$ | C$_2$H$_5$OCH$_2$ |
| 1-158 | H | Cl | CH$_3$ | CH$_3$OCH$_2$CH$_2$ |

TABLE 1-continued

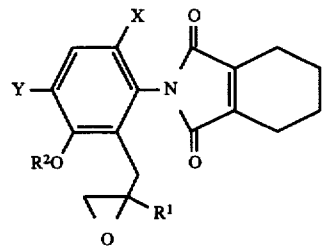

(compound wherein Q is Q-1.)

| Compound No. | X | Y | R¹ | R² |
|---|---|---|---|---|
| 1-159 | H | Cl | CH₃ | CH₃OCH₂CH₂OCH₂ |
| 1-160 | H | Cl | CH₃ | CH₃SCH₂ |
| 1-161 | H | Cl | CH₃ | CH₂=CHCH₂ |
| 1-162 | H | Cl | CH₃ | CH₂=CHCH₂CH₂ |
| 1-163 | H | Cl | CH₃ | CH₃—CH=CHCH₂ |
| 1-164 | H | Cl | CH₃ | CH₂=CClCH₂ |
| 1-165 | H | Cl | CH₃ | CCl₂=CHCH₂ |
| 1-166 | H | Cl | CH₃ | CH≡CCH₂ |
| 1-167 | H | Cl | CH₃ | CH≡CCH(CH₃) |
| 1-168 | H | Cl | CH₃ | BrC≡CCH₂ |
| 1-169 | H | Cl | CH₃ | cC₅H₉ |
| 1-170 | H | Cl | CH₃ | cC₆H₁₁ |
| 1-171 | H | Cl | CH₃ | CH₃CO |
| 1-172 | H | Cl | CH₃ | C₂H₅CO |
| 1-173 | H | Cl | CH₃ | (CH₃)₂CHCO |
| 1-174 | H | Cl | CH₃ | (CH₃)₃CCO |
| 1-175 | H | Cl | CH₃ | C₆H₅CO |
| 1-176 | H | Cl | CH₃ | p-CH₃OC₆H₄CO |
| 1-177 | H | Cl | CH₃ | p-CH₃C₆H₅CO |
| 1-178 | H | Cl | CH₃ | ClCH₂CO |
| 1-179 | H | Cl | CH₃ | CH₃NHCO |
| 1-180 | H | Cl | CH₃ | (CH₃)₂NCO |
| 1-181 | H | Cl | CH₃ | (C₂H₅)₂NCO |
| 1-182 | H | Cl | H | C₆H₅CH₂ |
| 1-183 | H | Cl | CH₃ | p-CH₃OC₆H₄CH₂ |
| 1-184 | H | Cl | CH₃ | p-ClC₆H₄CH₂ |
| 1-185 | H | Cl | CH₃ | C₆H₅CH₂CH₂ |
| 1-186 | H | Cl | CH₃ | CH₃OOCCH₂ |
| 1-187 | H | Cl | CH₃ | C₂H₅OOCCH₂ |
| 1-188 | H | Cl | CH₃ | (CH₃)₂CHOOCCH₂ |
| 1-189 | H | Cl | CH₃ | ⁿC₄H₉OOCCH₂ |
| 1-190 | H | Cl | CH₃ | ⁿC₅H₁₁OOCCH₂ |
| 1-191 | H | Cl | CH₃ | CH₃OOCCH(CH₃) |
| 1-192 | H | Cl | CH₃ | C₂H₅OOCCH(CH₃) |
| 1-193 | H | Cl | CH₃ | cC₅H₉OOCCH₂ |
| 1-194 | H | Cl | CH₃ | cC₆H₁₁OOCCH₂ |
| 1-195 | H | Cl | CH₃ | CH₃SO₂ |
| 1-196 | H | Cl | CH₃ | C₂H₅SO₂ |
| 1-197 | H | Cl | CH₃ | (CH₃)₂CHSO₂ |
| 1-198 | H | Cl | CH₃ | ClCH₂SO₂ |
| 1-199 | H | Cl | CH₃ | C₆H₅SO₂ |
| 1-200 | H | Cl | CH₃ | p-CH₃C₆H₄SO₂ |
| 1-201 | F | Br | H | (CH₃)₂CH |
| 1-202 | Cl | Cl | H | (CH₃)₂CH |
| 1-203 | F | F | H | (CH₃)₂CH |

TABLE 2

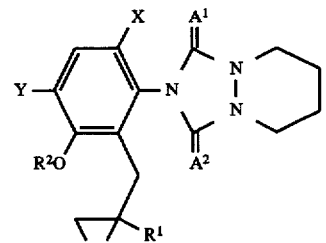

(compound wherein Q is Q-2.)

| Compound No. | X | Y | A¹ | A² | R¹ | R² |
|---|---|---|---|---|---|---|
| 2-1 | F | Cl | O | O | H | (CH₃)₂CH |
| 2-2 | F | Cl | O | O | H | ClCH₂CH₂ |
| 2-3 | F | Cl | O | O | H | CH₃OCH₂ |
| 2-4 | F | Cl | O | O | H | CH₃OCH₂CH₂OCH₂ |
| 2-5 | F | Cl | O | O | H | CH₃SCH₂ |
| 2-6 | F | Cl | O | O | H | CH₂=CHCH₂ |
| 2-7 | F | Cl | O | O | H | CH₂=CClCH₂ |
| 2-8 | F | Cl | O | O | H | CH≡CCH₂ |
| 2-9 | F | Cl | O | O | H | CH≡CCH(CH₃) |
| 2-10 | F | Cl | O | O | H | cC₅H₉ |
| 2-11 | F | Cl | O | O | H | CH₃CO |
| 2-12 | F | Cl | O | O | H | CH₃NHCO |
| 2-13 | F | Cl | O | O | H | C₆H₅CO |
| 2-14 | F | Cl | O | O | H | C₆H₅CH₂ |
| 2-15 | F | Cl | O | O | H | CH₃OOCCH₂ |
| 2-16 | F | Cl | O | O | H | CH₃SO₂ |
| 2-17 | F | Cl | O | O | CH₃ | (CH₃)₂CH |
| 2-18 | F | Cl | O | O | CH₃ | ClCH₂CH₂ |
| 2-19 | F | Cl | O | O | CH₃ | CH₃OCH₂ |
| 2-20 | F | Cl | O | O | CH₃ | CH₃OCH₂CH₂OCH₂ |
| 2-21 | F | Cl | O | O | CH₃ | CH₃SCH₂ |
| 2-22 | F | Cl | O | O | CH₃ | CH₂=CHCH₂ |
| 2-23 | F | Cl | O | O | CH₃ | CH₂=CClCH₂ |
| 2-24 | F | Cl | O | O | CH₃ | CH≡CCH₂ |
| 2-25 | F | Cl | O | O | CH₃ | CH≡CCH(CH₃) |
| 2-26 | F | Cl | O | O | CH₃ | cC₅H₉ |
| 2-27 | F | Cl | O | O | CH₃ | CH₃CO |
| 2-28 | F | Cl | O | O | CH₃ | CH₃NHCO |
| 2-29 | F | Cl | O | O | CH₃ | C₆H₅CO |
| 2-30 | F | Cl | O | O | CH₃ | C₆H₅CH₂ |
| 2-31 | F | Cl | O | O | CH₃ | CH₃OOCCH₂ |
| 2-32 | F | Cl | O | O | CH₃ | CH₃SO₂ |
| 2-33 | H | Cl | O | O | H | (CH₃)₂CH |
| 2-34 | H | Cl | O | O | H | ClCH₂CH₂ |
| 2-35 | F | Cl | O | O | H | CH₃OCH₂ |
| 2-36 | H | Cl | O | O | H | CH₃OCH₂CH₂OCH₂ |
| 2-37 | H | Cl | O | O | H | CH₃SCH₂ |
| 2-38 | H | Cl | O | O | H | CH₂=CHCH₂ |
| 2-39 | H | Cl | O | O | H | CH₂=CClCH₂ |
| 2-40 | H | Cl | O | O | H | CH≡CCH₂ |
| 2-41 | H | Cl | O | O | H | CH≡CCH(CH₃) |
| 2-42 | H | Cl | O | O | H | cC₅H₉ |
| 2-43 | H | Cl | O | O | H | CH₃CO |
| 2-44 | H | Cl | O | O | H | CH₃NHCO |
| 2-45 | H | Cl | O | O | H | C₆H₅CO |
| 2-46 | H | Cl | O | O | M | C₆H₅CH₂ |
| 2-47 | H | Cl | O | O | H | CH₃OOCCH₂ |
| 2-48 | H | Cl | O | O | H | CH₃SO₂ |
| 2-49 | H | Cl | O | O | CH₃ | (CH₃)₂CH |
| 2-50 | H | Cl | O | O | CH₃ | ClCH₂CH₂ |
| 2-51 | H | Cl | O | O | CH₃ | CH₃OCH₂ |
| 2-52 | H | Cl | O | O | CH₃ | CH₃OCH₂CH₂OCH₂ |
| 2-53 | H | Cl | O | O | CH₃ | CH₃SCH₂ |
| 2-54 | H | Cl | O | O | CH₃ | CH₂=CHCH₂ |
| 2-55 | H | Cl | O | O | CH₃ | CH₂=CClCH₂ |

TABLE 2-continued

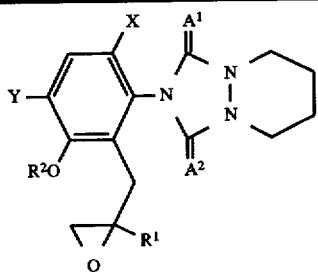

(compound wherein Q is Q-2.)

| Compound No. | X | Y | $A^1$ | $A^2$ | $R^1$ | $R^2$ |
|---|---|---|---|---|---|---|
| 2-56 | H | Cl | O | O | $CH_3$ | $CH\equiv CCH_2$ |
| 2-57 | H | Cl | O | O | $CH_3$ | $CH\equiv CCH(CH_3)$ |
| 2-58 | H | Cl | O | O | $CH_3$ | $cC_5H_9$ |
| 2-59 | H | Cl | O | O | $CH_3$ | $CH_3CO$ |
| 2-60 | H | Cl | O | O | $CH_3$ | $CH_3NHCO$ |
| 2-61 | H | Cl | O | O | $CH_3$ | $C_6H_5CO$ |
| 2-62 | H | Cl | O | O | $CH_3$ | $C_6H_5CH_2$ |
| 2-63 | H | Cl | O | O | $CH_3$ | $CH_3OOCCH_2$ |
| 2-64 | H | Cl | O | O | $CH_3$ | $CH_3SO_2$ |
| 2-65 | F | Cl | S | O | $CH_3$ | $(CH_3)_2CH$ |
| 2-66 | F | Br | O | O | $CH_3$ | $(CH_3)_2CH$ |
| 2-67 | F | F | O | O | $CH_3$ | $(CH_3)_2CH$ |
| 2-68 | Cl | Cl | O | O | $CH_3$ | $(CH_3)_2CH$ |

TABLE 3

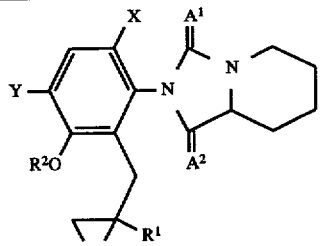

(compound wherein Q is Q-3.)

| Compound No. | X | Y | $A^1$ | $A^2$ | $R^1$ | $R^2$ |
|---|---|---|---|---|---|---|
| 3-1 | F | Cl | O | O | H | $(CH_3)_2CH$ |
| 3-2 | F | Cl | O | O | H | $ClCH_2CH_2$ |
| 3-3 | F | Cl | O | O | H | $CH_3OCH_2$ |
| 3-4 | F | Cl | O | O | H | $CH_3OCH_2CH_2OCH_2$ |
| 3-5 | F | Cl | O | O | H | $CH_3SCH_2$ |
| 3-6 | F | Cl | O | O | H | $CH_2=CHCH_2$ |
| 3-7 | F | Cl | O | O | H | $CH_2=CClCH_2$ |
| 3-8 | F | Cl | O | O | H | $CH\equiv CCH_2$ |
| 3-9 | F | Cl | O | O | H | $CH\equiv CCH(CH_3)$ |
| 3-10 | F | Cl | O | O | H | $cC_5H_9$ |
| 3-11 | F | Cl | O | O | H | $CH_3CO$ |
| 3-12 | F | Cl | O | O | H | $CH_3NHCO$ |
| 3-13 | F | Cl | O | O | H | $C_6H_5CO$ |
| 3-14 | F | Cl | O | O | H | $C_6H_5CH_2$ |
| 3-15 | F | Cl | O | O | H | $CH_3OOCCH_2$ |
| 3-16 | F | Cl | O | O | H | $CH_3SO_2$ |
| 3-17 | F | Cl | O | O | $CH_3$ | $(CH_3)_2CH$ |
| 3-18 | F | Cl | O | O | $CH_3$ | $ClCH_2CH_2$ |
| 3-19 | F | Cl | O | O | $CH_3$ | $CH_3OCH_2$ |
| 3-20 | F | Cl | O | O | $CH_3$ | $CH_3OCH_2CH_2OCH_2$ |
| 3-21 | F | Cl | O | O | $CH_3$ | $CH_3SCH_2$ |
| 3-22 | F | Cl | O | O | $CH_3$ | $CH_2=CHCH_2$ |

TABLE 3-continued

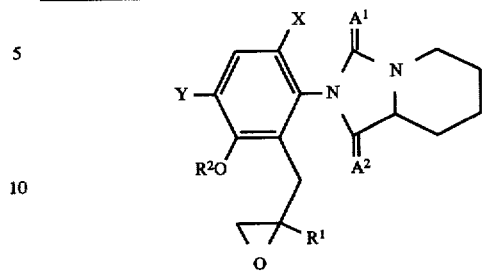

(compound wherein Q is Q-3.)

| Compound No. | X | Y | $A^1$ | $A^2$ | $R^1$ | $R^2$ |
|---|---|---|---|---|---|---|
| 3-23 | F | Cl | O | O | $CH_3$ | $CH_2=CClCH_2$ |
| 3-24 | F | Cl | O | O | $CH_3$ | $CH\equiv CCH_2$ |
| 3-25 | F | Cl | O | O | $CH_3$ | $CH\equiv CCH(CH_3)$ |
| 3-26 | F | Cl | O | O | $CH_3$ | $cC_5H_9$ |
| 3-27 | F | Cl | O | O | $CH_3$ | $CH_3CO$ |
| 3-28 | F | Cl | O | O | $CH_3$ | $CH_3NHCO$ |
| 3-29 | F | Cl | O | O | $CH_3$ | $C_6H_5CO$ |
| 3-30 | F | Cl | O | O | $CH_3$ | $C_6H_5CH_2$ |
| 3-31 | F | Cl | O | O | $CH_3$ | $CH_3OOCCH_2$ |
| 3-32 | F | Cl | O | O | $CH_3$ | $CH_3SO_2$ |
| 3-33 | H | Cl | O | O | H | $(CH_3)_2CH$ |
| 3-34 | H | Cl | O | O | H | $ClCH_2CH_2$ |
| 3-35 | F | Cl | O | O | H | $CH_3OCH_2$ |
| 3-36 | H | Cl | O | O | H | $CH_3OCH_2CH_2OCH_2$ |
| 3-37 | H | Cl | O | O | H | $CH_3SCH_2$ |
| 3-38 | H | Cl | O | O | H | $CH_2=CHCH_2$ |
| 3-39 | H | Cl | O | O | H | $CH_2=CClCH_2$ |
| 3-40 | H | Cl | O | O | H | $CH\equiv CCH_2$ |
| 3-41 | H | Cl | O | O | H | $CH\equiv CCH(CH_3)$ |
| 3-42 | H | Cl | O | O | H | $cC_5H_9$ |
| 3-43 | H | Cl | O | O | H | $CH_3CO$ |
| 3-44 | H | Cl | O | O | H | $CH_3NHCO$ |
| 3-45 | H | Cl | O | O | H | $C_6H_5CO$ |
| 3-46 | H | Cl | O | O | H | $C_6H_5CH_2$ |
| 3-47 | H | Cl | O | O | H | $CH_3OOCCH_2$ |
| 3-48 | H | Cl | O | O | H | $CH_3SO_2$ |
| 3-49 | H | Cl | O | O | $CH_3$ | $(CH_3)_2CH$ |
| 3-50 | H | Cl | O | O | $CH_3$ | $ClCH_2CH_2$ |
| 3-51 | H | Cl | O | O | $CH_3$ | $CH_3OCH_2$ |
| 3-52 | H | Cl | O | O | $CH_3$ | $CH_3OCH_2CH_2OCH_2$ |
| 3-53 | H | Cl | O | O | $CH_3$ | $CH_3SCH_2$ |
| 3-54 | H | Cl | O | O | $CH_3$ | $CH_2=CHCH_2$ |
| 3-55 | H | Cl | O | O | $CH_3$ | $CH_2=CClCH_2$ |
| 3-56 | H | Cl | O | O | $CH_3$ | $CH\equiv CCH_2$ |
| 3-57 | H | Cl | O | O | $CH_3$ | $CH\equiv CCH(CH_3)$ |
| 3-58 | H | Cl | O | O | $CH_3$ | $cC_5H_9$ |
| 3-59 | H | Cl | O | O | $CH_3$ | $CH_3CO$ |
| 3-60 | H | Cl | O | O | $CH_3$ | $CH_3NHCO$ |
| 3-61 | H | Cl | O | O | $CH_3$ | $C_6H_5CO$ |
| 3-62 | H | Cl | O | O | $CH_3$ | $C_6H_5CH_2$ |
| 3-63 | H | Cl | O | O | $CH_3$ | $CH_3OOCCH_2$ |
| 3-64 | H | Cl | O | O | $CH_3$ | $CH_3SO_2$ |
| 3-65 | F | Cl | S | O | $CH_3$ | $(CH_3)_2CH$ |
| 3-66 | F | Br | O | O | $CH_3$ | $(CH_3)_2CH$ |
| 3-67 | F | F | O | O | $CH_3$ | $(CH_3)_2CH$ |
| 3-68 | Cl | Cl | O | O | $CH_3$ | $(CH_3)_2CH$ |

TABLE 4

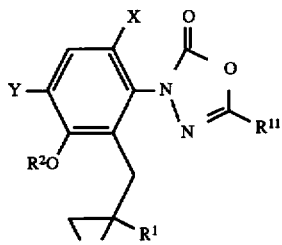

(compound wherein Q is Q-4.)

| Compound No. | X | Y | R[11] | R[1] | R[12] |
|---|---|---|---|---|---|
| 4-1 | F | Cl | (CH$_3$)$_3$C | H | (CH$_3$)$_2$CH |
| 4-2 | F | Cl | (CH$_3$)$_3$C | H | ClCH$_2$CH$_2$ |
| 4-3 | F | Cl | (CH$_3$)$_3$C | H | CH$_3$OCH$_2$ |
| 4-4 | F | Cl | (CH$_3$)$_3$C | H | CH$_3$OCH$_2$CH$_2$OCH$_2$ |
| 4-5 | F | Cl | (CH$_3$)$_3$C | H | CH$_3$SCH$_2$ |
| 4-6 | F | Cl | (CH$_3$)$_3$C | H | CH$_2$=CHCH$_2$ |
| 4-7 | F | Cl | (CH$_3$)$_3$C | H | CH$_2$=CClCH$_2$ |
| 4-8 | F | Cl | (CH$_3$)$_3$C | H | CH≡CCH$_2$ |
| 4-9 | F | Cl | (CH$_3$)$_3$C | H | CH≡CCH(CH$_3$) |
| 4-10 | F | Cl | (CH$_3$)$_3$C | H | cC$_5$H$_9$ |
| 4-11 | F | Cl | (CH$_3$)$_3$C | H | CH$_3$CO |
| 4-12 | F | Cl | (CH$_3$)$_3$C | H | CH$_3$NHCO |
| 4-13 | F | Cl | (CH$_3$)$_3$C | H | C$_6$H$_5$CO |
| 4-14 | F | Cl | (CH$_3$)$_3$C | H | C$_6$H$_5$CH$_2$ |
| 4-15 | F | Cl | (CH$_3$)$_3$C | H | CH$_3$OOCCH$_2$ |
| 4-16 | F | Cl | (CH$_3$)$_3$C | H | CH$_3$SO$_2$ |
| 4-17 | F | Cl | (CH$_3$)$_3$C | CH$_3$ | (CH$_3$)$_2$CH |
| 4-18 | F | Cl | (CH$_3$)$_3$C | CH$_3$ | ClCH$_2$CH$_2$ |
| 4-19 | F | Cl | (CH$_3$)$_3$C | CH$_3$ | CH$_3$OCH$_2$ |
| 4-20 | F | Cl | (CH$_3$)$_3$C | CH$_3$ | CH$_3$OCH$_2$CH$_2$OCH$_2$ |
| 4-21 | F | Cl | (CH$_3$)$_3$C | CH$_3$ | CH$_3$SCH$_2$ |
| 4-22 | F | Cl | (CH$_3$)$_3$C | CH$_3$ | CH$_2$=CHCH$_2$ |
| 4-23 | F | Cl | (CH$_3$)$_3$C | CH$_3$ | CH$_2$=CClCH$_2$ |
| 4-24 | F | Cl | (CH$_3$)$_3$C | CH$_3$ | CH≡CCH$_2$ |
| 4-25 | F | Cl | (CH$_3$)$_3$C | CH$_3$ | CH≡CCH(CH$_3$) |
| 4-26 | F | Cl | (CH$_3$)$_3$C | CH$_3$ | cC$_5$H$_9$ |
| 4-27 | F | Cl | (CH$_3$)$_3$C | CH$_3$ | CH$_3$CO |
| 4-28 | F | Cl | (CH$_3$)$_3$C | CH$_3$ | CH$_3$NHCO |
| 4-29 | F | Cl | (CH$_3$)$_3$C | CH$_3$ | C$_6$H$_5$CO |
| 4-30 | F | Cl | (CH$_3$)$_3$C | CH$_3$ | C$_6$H$_5$CH$_2$ |
| 4-31 | F | Cl | (CH$_3$)$_3$C | CH$_3$ | CH$_3$OOCCH$_2$ |
| 4-32 | F | Cl | (CH$_3$)$_3$C | CH$_3$ | CH$_3$SO$_2$ |
| 4-33 | H | Cl | (CH$_3$)$_3$C | H | (CH$_3$)$_2$CH |
| 4-34 | H | Cl | (CH$_3$)$_3$C | H | ClCH$_2$CH$_2$ |
| 4-35 | H | Cl | (CH$_3$)$_3$C | H | CH$_3$OCH$_2$ |
| 4-36 | H | Cl | (CH$_3$)$_3$C | H | CH$_3$OCH$_2$CH$_2$OCH$_2$ |
| 4-37 | H | Cl | (CH$_3$)$_3$C | H | CH$_3$SCH$_2$ |
| 4-38 | H | Cl | (CH$_3$)$_3$C | H | CH$_2$=CHCH$_2$ |
| 4-39 | H | Cl | (CH$_3$)$_3$C | H | CH$_2$=CClCH$_2$ |
| 4-40 | H | Cl | (CH$_3$)$_3$C | H | CH≡CCH$_2$ |
| 4-41 | H | Cl | (CH$_3$)$_3$C | H | CH≡CCH(CH$_3$) |
| 4-42 | H | Cl | (CH$_3$)$_3$C | H | cC$_5$H$_9$ |
| 4-43 | H | Cl | (CH$_3$)$_3$C | H | CH$_3$CO |
| 4-44 | H | Cl | (CH$_3$)$_3$C | H | CH$_3$NHCO |
| 4-45 | H | Cl | (CH$_3$)$_3$C | H | C$_6$H$_5$CO |
| 4-46 | H | Cl | (CH$_3$)$_3$C | H | C$_6$H$_5$CH$_2$ |
| 4-47 | H | Cl | (CH$_3$)$_3$C | H | CH$_3$OOCCH$_2$ |
| 4-48 | H | Cl | (CH$_3$)$_3$C | H | CH$_3$SO$_2$ |
| 4-49 | H | Cl | (CH$_3$)$_3$C | CH$_3$ | (CH$_3$)$_2$CH |
| 4-50 | H | Cl | (CH$_3$)$_3$C | CH$_3$ | ClCH$_2$CH$_2$ |
| 4-51 | H | Cl | (CH$_3$)$_3$C | CH$_3$ | CH$_3$OCH$_2$ |
| 4-52 | H | Cl | (CH$_3$)$_3$C | CH$_3$ | CH$_3$OCH$_2$CH$_2$OCH$_2$ |
| 4-53 | H | Cl | (CH$_3$)$_3$C | CH$_3$ | CH$_3$SCH$_2$ |
| 4-54 | H | Cl | (CH$_3$)$_3$C | CH$_3$ | CH$_2$=CHCH$_2$ |
| 4-55 | H | Cl | (CH$_3$)$_3$C | CH$_3$ | CH$_2$=CClCH$_2$ |
| 4-56 | H | Cl | (CH$_3$)$_3$CH | CH$_3$ | CH≡CCH$_2$ |
| 4-57 | H | Cl | (CH$_3$)$_3$C | CH$_3$ | CH≡CCH(CH$_3$) |
| 4-58 | H | Cl | (CH$_3$)$_3$C | CH$_3$ | cC$_5$H$_9$ |
| 4-59 | H | Cl | (CH$_3$)$_3$C | CH$_3$ | CH$_3$CO |
| 4-60 | H | Cl | (CH$_3$)$_3$C | CH$_3$ | CH$_3$NHCO |
| 4-61 | H | Cl | (CH$_3$)$_3$C | CH$_3$ | C$_6$H$_5$CO |
| 4-62 | H | Cl | (CH$_3$)$_3$C | CH$_3$ | C$_6$H$_5$CH$_2$ |
| 4-63 | H | Cl | (CH$_3$)$_3$C | CH$_3$ | CH$_3$OOCCH$_2$ |
| 4-64 | H | Cl | (CH$_3$)$_3$C | CH$_3$ | CH$_3$SO$_2$ |
| 4-65 | Cl | Cl | (CH$_3$)$_3$C | CH$_3$ | (CH$_3$)$_2$CH |
| 4-66 | F | Cl | CH$_3$ | CH$_3$ | (CH$_3$)$_2$CH |
| 4-67 | F | Cl | (CH$_3$)$_3$C | CH$_3$ | (CH$_3$)$_2$CH |
| 4-68 | F | Br | (CH$_3$)$_3$C | CH$_3$ | (CH$_3$)$_2$CH |
| 4-69 | F | F | (CH$_3$)$_3$C | CH$_3$ | (CH$_3$)$_2$CH |

TABLE 5

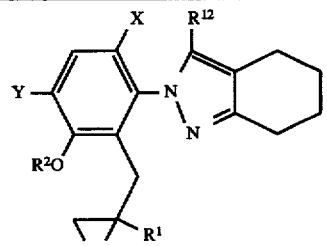

(compound wherein Q is Q-5.)

| Compound No. | X | Y | R[12] | R[1] | R[2] |
|---|---|---|---|---|---|
| 5-1 | F | Cl | Cl | H | (CH$_3$)$_2$CH |
| 5-2 | F | Cl | Cl | H | ClCH$_2$CH$_2$ |
| 5-3 | F | Cl | Cl | H | CH$_3$OCH$_2$ |
| 5-4 | F | Cl | Cl | H | CH$_3$OCH$_2$CH$_2$OCH$_2$ |
| 5-5 | F | Cl | Cl | H | CH$_3$SCH$_2$ |
| 5-6 | F | Cl | Cl | H | CH$_2$=CHCH$_2$ |
| 5-7 | F | Cl | Cl | H | CH$_2$=CClCH$_2$ |
| 5-8 | F | Cl | Cl | H | CH≡CCH$_2$ |
| 5-9 | F | Cl | Cl | H | CH≡CCH(CH$_3$) |
| 5-10 | F | Cl | Cl | H | cC$_5$H$_9$ |
| 5-11 | F | Cl | Cl | H | CH$_3$CO |
| 5-12 | F | Cl | Cl | H | CH$_3$NHCO |
| 5-13 | F | Cl | Cl | H | C$_6$H$_5$CO |
| 5-14 | F | Cl | Cl | H | C$_6$H$_5$CH$_2$ |
| 5-15 | F | Cl | Cl | H | CH$_3$OOCCH$_2$ |
| 5-16 | F | Cl | Cl | H | CH$_3$SO$_2$ |
| 5-17 | F | Cl | Cl | CH$_3$ | (CH$_3$)$_2$CH |
| 5-18 | F | Cl | Cl | CH$_3$ | ClCH$_2$CH$_2$ |
| 5-19 | F | Cl | Cl | CH$_3$ | CH$_3$OCH$_2$ |
| 5-20 | F | Cl | Cl | CH$_3$ | CH$_3$OCH$_2$CH$_2$OCH$_2$ |
| 5-21 | F | Cl | Cl | CH$_3$ | CH$_3$SCH$_2$ |

TABLE 5-continued

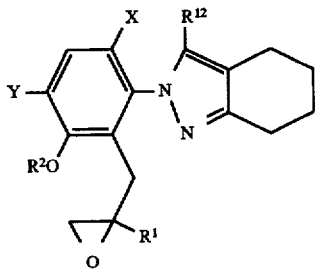

(compound wherein Q is Q-5.)

| Compound No. | X | Y | R12 | R1 | R2 |
|---|---|---|---|---|---|
| 5-22 | F | Cl | Cl | CH3 | CH2=CHCH2 |
| 5-23 | F | Cl | Cl | CH3 | CH2=CClCH2 |
| 5-24 | F | Cl | Cl | CH3 | CH≡CCH2 |
| 5-25 | F | Cl | Cl | CH3 | CH≡CCH(CH3) |
| 5-26 | F | Cl | Cl | CH3 | cC5H9 |
| 5-27 | F | Cl | Cl | CH3 | CH3CO |
| 5-28 | F | Cl | Cl | CH3 | CH3NHCO |
| 5-29 | F | Cl | Cl | CH3 | C6H5CO |
| 5-30 | F | Cl | Cl | CH3 | C6H5CH2 |
| 5-31 | F | Cl | Cl | CH3 | CH3OOCCH2 |
| 5-32 | F | Cl | Cl | CH3 | CH3SO2 |
| 5-33 | H | Cl | Cl | H | (CH3)2CH |
| 5-34 | H | Cl | Cl | H | ClCH2CH2 |
| 5-35 | H | Cl | Cl | H | CH3OCH2 |
| 5-36 | H | Cl | Cl | H | CH3OCH2CH2OCH2 |
| 5-37 | H | Cl | Cl | H | CH3SCH2 |
| 5-38 | H | Cl | Cl | H | CH2=CHCH2 |
| 5-39 | H | Cl | Cl | H | CH2=CClCH2 |
| 5-40 | H | Cl | Cl | H | CH≡CCH2 |
| 5-41 | H | Cl | Cl | H | CH≡CCH(CH3) |
| 5-42 | H | Cl | Cl | H | cC5H9 |
| 5-43 | H | Cl | Cl | H | CH3CO |
| 5-44 | H | Cl | Cl | H | CH3NHCO |
| 5-45 | H | Cl | Cl | H | C6H5CO |
| 5-46 | H | Cl | Cl | H | C6H5CH2 |
| 5-47 | H | Cl | Cl | H | CH3OOCCH2 |
| 5-48 | H | Cl | Cl | H | CH3SO2 |
| 5-49 | H | Cl | Cl | CH3 | (CH3)2CH |
| 5-50 | H | Cl | Cl | CH3 | ClCH2CH2 |
| 5-51 | H | Cl | Cl | CH3 | CH3OCH2 |
| 5-52 | H | Cl | Cl | CH3 | CH3OCH2CH2OCH2 |
| 5-53 | H | Cl | Cl | CH3 | CH3SCH2 |
| 5-54 | H | Cl | Cl | CH3 | CH2=CHCH2 |
| 5-55 | H | Cl | Cl | CH3 | CH2=CClCH2 |
| 5-56 | H | Cl | Cl | CH3 | CH≡CCH2 |
| 5-57 | H | Cl | Cl | CH3 | CH≡CCH(CH3) |
| 5-58 | H | Cl | Cl | CH3 | cC5H9 |
| 5-59 | H | Cl | Cl | CH3 | CH3CO |
| 5-60 | H | Cl | Cl | CH3 | CH3NHCO |
| 5-61 | H | Cl | Cl | CH3 | C6H5CO |
| 5-62 | H | Cl | Cl | CH3 | C6H5CH2 |
| 5-63 | H | Cl | Cl | CH3 | CH3OOCCH2 |
| 5-64 | H | Cl | Cl | CH3 | CH3SO2 |
| 5-65 | F | Br | Cl | H | (CH3)2CH |
| 5-66 | F | F | Cl | H | (CH3)2CH |
| 5-67 | Cl | Cl | Cl | H | (CH3)2CH |
| 5-68 | F | Cl | OCH3 | H | (CH3)2CH |
| 5-69 | F | Cl | CH3 | H | (CH3)2CH |

TABLE 6

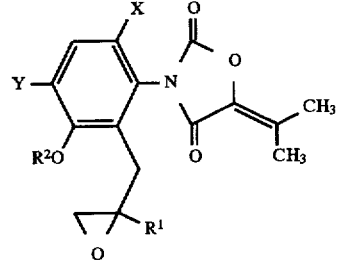

(compound wherein Q is Q-6.)

| Compound No. | X | Y | R1 | R2 |
|---|---|---|---|---|
| 6-1 | F | Cl | H | (CH3)2CH |
| 6-2 | F | Cl | H | ClCH2CH2 |
| 6-3 | F | Cl | H | CH3OCH2 |
| 6-4 | F | Cl | H | CH3OCH2CH2OCH2 |
| 6-5 | F | Cl | H | CH3SCH2 |
| 6-6 | F | Cl | H | CH2=CHCH2 |
| 6-7 | F | Cl | H | CH2=CClCH2 |
| 6-8 | F | Cl | H | CH≡CCH2 |
| 6-9 | F | Cl | H | CH≡CCH(CH3) |
| 6-10 | F | Cl | H | cC5H9 |
| 6-11 | F | Cl | H | CH3CO |
| 6-12 | F | Cl | H | CH3NHCO |
| 6-13 | F | Cl | H | C6H5CO |
| 6-14 | F | Cl | H | C6H5CH2 |
| 6-15 | F | Cl | H | CH3OOCCH2 |
| 6-16 | F | Cl | H | CH3SO2 |
| 6-17 | F | Cl | CH3 | (CH3)2CH |
| 6-18 | F | Cl | CH3 | ClCH2CH2 |
| 6-19 | F | Cl | CH3 | CH3OCH2 |
| 6-20 | F | Cl | CH3 | CH3OCH2CH2OCH2 |
| 6-21 | F | Cl | CH3 | CH3SCH2 |
| 6-22 | F | Cl | CH3 | CH2=CHCH2 |
| 6-23 | F | Cl | CH3 | CH2=CClCH2 |
| 6-24 | F | Cl | CH3 | CH≡CCH2 |
| 6-25 | F | Cl | CH3 | CH≡CCH(CH3) |
| 6-26 | F | Cl | CH3 | cC5H9 |
| 6-27 | F | Cl | CH3 | CH3CO |
| 6-28 | F | Cl | CH3 | CH3NHCO |
| 6-29 | F | Cl | CH3 | C6H5CO |
| 6-30 | F | Cl | CH3 | C6H5CH2 |
| 6-31 | F | Cl | CH3 | CH3OOCCH2 |
| 6-32 | F | Cl | CH3 | CH3SO2 |
| 6-33 | H | Cl | H | (CH3)2CH |
| 6-34 | H | Cl | H | ClCH2CH2 |
| 6-35 | H | Cl | H | CH3OCH2 |
| 6-36 | H | Cl | H | CH3OCH2CH2OCH2 |
| 6-37 | H | Cl | H | CH3SCH2 |
| 6-38 | H | Cl | H | CH2=CHCH2 |
| 6-39 | H | Cl | H | CH2=CClCH2 |
| 6-40 | H | Cl | H | CH≡CCH2 |
| 6-41 | H | Cl | H | CH≡CCH(CH3) |
| 6-42 | H | Cl | H | cC5H9 |
| 6-43 | H | Cl | H | CH3CO |
| 6-44 | H | Cl | H | CH3NHCO |
| 6-45 | H | Cl | H | C6H5CO |
| 6-46 | H | Cl | H | C6H5CH2 |
| 6-47 | H | Cl | H | CH3OOCCH2 |
| 6-48 | H | Cl | H | CH3SO2 |
| 6-49 | H | Cl | CH3 | (CH3)2CH |
| 6-50 | H | Cl | CH3 | ClCH2CH2 |
| 6-51 | H | Cl | CH3 | CH3OCH2 |
| 6-52 | H | Cl | CH3 | CH3OCH2CH2OCH2 |
| 6-53 | H | Cl | CH3 | CH3SCH2 |
| 6-54 | H | Cl | CH3 | CH2=CHCH2 |
| 6-55 | H | Cl | CH3 | CH2=CClCH2 |

TABLE 6-continued (compound wherein Q is Q-6.)

| Compound No. | X | Y | R¹ | R² |
|---|---|---|---|---|
| 6-56 | H | Cl | CH₃ | CH≡CCH₂ |
| 6-57 | H | Cl | CH₃ | CH≡CCH(CH₃) |
| 6-58 | H | Cl | CH₃ | cC₅H₉ |
| 6-59 | H | Cl | CH₃ | CH₃CO |
| 6-60 | H | Cl | CH₃ | CH₃NHCO |
| 6-61 | H | Cl | CH₃ | C₆H₅CO |
| 6-62 | H | Cl | CH₃ | C₆H₅CH₂ |
| 6-63 | H | Cl | CH₃ | CH₃OOCCH₂ |
| 6-64 | H | Cl | CH₃ | CH₃SO₂ |
| 6-65 | F | Br | H | (CH₃)₂CH |
| 6-66 | F | F | H | (CH₃)₂CH |
| 6-67 | Cl | Cl | H | (CH₃)₂CH |

TABLE 7

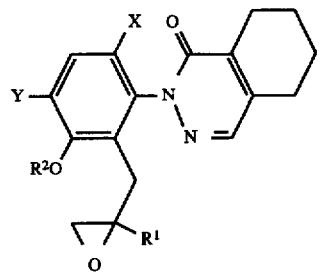

(compound wherein Q is Q-7.)

| Compound No. | X | Y | R¹ | R² |
|---|---|---|---|---|
| 7-1 | F | Cl | H | (CH₃)₂CH |
| 7-2 | F | Cl | H | ClCH₂CH₂ |
| 7-3 | F | Cl | H | CH₃OCH₂ |
| 7-4 | F | Cl | H | CH₃OCH₂CH₂OCH₂ |
| 7-5 | F | Cl | H | CH₃SCH₂ |
| 7-6 | F | Cl | H | CH₂=CHCH₂ |
| 7-7 | F | Cl | H | CH₂=CClCH₂ |
| 7-8 | F | Cl | H | CH≡CCH₂ |
| 7-9 | F | Cl | H | CH≡CCH(CH₃) |
| 7-10 | F | Cl | H | cC₅H₉ |
| 7-11 | F | Cl | H | CH₃CO |
| 7-12 | F | Cl | H | CH₃NHCO |
| 7-13 | F | Cl | H | C₆H₅CO |
| 7-14 | F | Cl | H | C₆H₅CH₂ |
| 7-15 | F | Cl | H | CH₃OOCCH₂ |
| 7-16 | F | Cl | H | CH₃SO₂ |
| 7-17 | F | Cl | CH₃ | (CH₃)₂CH |
| 7-18 | F | Cl | CH₃ | ClCH₂CH₂ |
| 7-19 | F | Cl | CH₃ | CH₃OCH₂ |
| 7-20 | F | Cl | CH₃ | CH₃OCH₂CH₂OCH₂ |
| 7-21 | F | Cl | CH₃ | CH₃SCH₂ |
| 7-22 | F | Cl | CH₃ | CH₂=CHCH₂ |
| 7-23 | F | Cl | CH₃ | CH₂=CClCH₂ |

TABLE 7-continued (compound wherein Q is Q-7.)

| Compound No. | X | Y | R¹ | R² |
|---|---|---|---|---|
| 7-24 | F | Cl | CH₃ | CH≡CCH₂ |
| 7-25 | F | Cl | CH₃ | CH≡CCH(CH₃) |
| 7-26 | F | Cl | CH₃ | cC₅H₉ |
| 7-27 | F | Cl | CH₃ | CH₃CO |
| 7-28 | F | Cl | CH₃ | CH₃NHCO |
| 7-29 | F | Cl | CH₃ | C₆H₅CO |
| 7-30 | F | Cl | CH₃ | C₆H₅CH₂ |
| 7-31 | F | Cl | CH₃ | CH₃OOCCH₂ |
| 7-32 | F | Cl | CH₃ | CH₃SO₂ |
| 7-33 | H | Cl | H | (CH₃)₂CH |
| 7-34 | H | Cl | H | ClCH₂CH₂ |
| 7-35 | H | Cl | H | CH₃OCH₂ |
| 7-36 | H | Cl | H | CH₃OCH₂CH₂OCH₂ |
| 7-37 | H | Cl | H | CH₃SCH₂ |
| 7-38 | H | Cl | H | CH₂=CHCH₂ |
| 7-39 | H | Cl | H | CH₂=CClCH₂ |
| 7-40 | H | Cl | H | CH≡CCH₂ |
| 7-41 | H | Cl | H | CH≡CCH(CH₃) |
| 7-42 | H | Cl | H | cC₅H₉ |
| 7-43 | H | Cl | H | CH₃CO |
| 7-44 | H | Cl | H | CH₃NHCO |
| 7-45 | H | Cl | H | C₆H₅CO |
| 7-46 | H | Cl | H | C₆H₅CH₂ |
| 7-47 | H | Cl | H | CH₃OOCCH₂ |
| 7-48 | H | Cl | H | CH₃SO₂ |
| 7-49 | H | Cl | CH₃ | (CH₃)₂CH |
| 7-50 | H | Cl | CH₃ | ClCH₂CH₂ |
| 7-51 | H | Cl | CH₃ | CH₃OCH₂ |
| 7-52 | H | Cl | CH₃ | CH₃OCH₂CH₂OCH₂ |
| 7-53 | H | Cl | CH₃ | CH₃SCH₂ |
| 7-54 | H | Cl | CH₃ | CH₂=CHCH₂ |
| 7-55 | H | Cl | CH₃ | CH₂=CClCH₂ |
| 7-56 | H | Cl | CH₃ | CH≡CCH₂ |
| 7-57 | H | Cl | CH₃ | CH≡CCH(CH₃) |
| 7-58 | H | Cl | CH₃ | cC₅H₉ |
| 7-59 | H | Cl | CH₃ | CH₃CO |
| 7-60 | H | Cl | CH₃ | CH₃NHCO |
| 7-61 | H | Cl | CH₃ | C₆H₅CO |
| 7-62 | H | Cl | CH₃ | C₆H₅CH₂ |
| 7-63 | H | Cl | CH₃ | CH₃OOCCH₂ |
| 7-64 | H | Cl | CH₃ | CH₃SO₂ |
| 7-65 | F | Br | H | (CH₃)₂CH |
| 7-66 | F | F | H | (CH₃)₂CH |
| 7-67 | Cl | Cl | H | (CH₃)₂CH |

TABLE 8

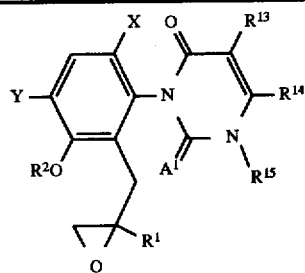

(compound wherein Q is Q-8.)

| Compound No. | X | Y | $A^1$ | $R^{13}$ | $R^{14}$ | $R^{15}$ | $R^1$ | $R^2$ |
|---|---|---|---|---|---|---|---|---|
| 8-1 | F | Cl | O | H | $CF_3$ | $CH_3$ | H | $CH_3$ |
| 8-2 | F | Cl | O | H | $CF_3$ | $CH_3$ | H | $C_2H_5$ |
| 8-3 | F | Cl | O | H | $CF_3$ | $CH_3$ | H | $(CH_3)_2CH$ |
| 8-4 | F | Cl | O | H | $CF_3$ | $CH_3$ | H | $(CH_3)_3C$ |
| 8-5 | F | Cl | O | H | $CF_3$ | $CH_3$ | H | $ClCH_2CH_2$ |
| 8-6 | F | Cl | O | H | $CF_3$ | $CH_3$ | H | $CH_3OCH_2$ |
| 8-7 | F | Cl | O | H | $CF_3$ | $CH_3$ | H | $C_2H_5OCH_2$ |
| 8-8 | F | Cl | O | H | $CF_3$ | $CH_3$ | H | $CH_3OCH_2CH_2$ |
| 8-9 | F | Cl | O | H | $CF_3$ | $CH_3$ | H | $CH_3OCH_2CH_2OCH_2$ |
| 8-10 | F | Cl | O | H | $CF_3$ | $CH_3$ | H | $CH_3SCH_2$ |
| 8-11 | F | Cl | O | H | $CF_3$ | $CH_3$ | H | $CH_2=CHCH_2$ |
| 8-12 | F | Cl | O | H | $CF_3$ | $CH_3$ | H | $CH_2=CHCH_2CH_2$ |
| 8-13 | F | Cl | O | H | $CF_3$ | $CH_3$ | H | $CH_3-CH=CHCH_2$ |
| 8-14 | F | Cl | O | H | $CF_3$ | $CH_3$ | H | $CH_2=CClCH_2$ |
| 8-15 | F | Cl | O | H | $CF_3$ | $CH_3$ | H | $CCl_2=CHCH_2$ |
| 8-16 | F | Cl | O | H | $CF_3$ | $CH_3$ | H | $CH\equiv CCH_2$ |
| 8-17 | F | Cl | O | H | $CF_3$ | $CH_3$ | H | $CH\equiv CCH(CH_3)$ |
| 8-18 | F | Cl | O | H | $CF_3$ | $CH_3$ | H | $BrC\equiv CCH_2$ |
| 8-19 | F | Cl | O | H | $CF_3$ | $CH_3$ | H | $cC_5H_9$ |
| 8-20 | F | Cl | O | H | $CF_3$ | $CH_3$ | H | $cC_6H_{11}$ |
| 8-21 | F | Cl | O | H | $CF_3$ | $CH_3$ | H | $CH_3CO$ |
| 8-22 | F | Cl | O | H | $CF_3$ | $CH_3$ | H | $C_2H_5CO$ |
| 8-23 | F | Cl | O | H | $CF_3$ | $CH_3$ | H | $(CH_3)_2CHCO$ |
| 8-24 | F | Cl | O | H | $CF_3$ | $CH_3$ | H | $(CH_3)_3CCO$ |
| 8-25 | F | Cl | O | H | $CF_3$ | $CH_3$ | H | $C_6H_5CO$ |
| 8-26 | F | Cl | O | H | $CF_3$ | $CH_3$ | H | $p\text{-}CH_3OC_6H_4CO$ |
| 8-27 | F | Cl | O | H | $CF_3$ | $CH_3$ | H | $p\text{-}CH_3C_6H_5CO$ |
| 8-28 | F | Cl | O | H | $CF_3$ | $CH_3$ | H | $ClCH_2CO$ |
| 8-29 | F | Cl | O | H | $CF_3$ | $CH_3$ | H | $CH_3NHCO$ |
| 8-30 | F | Cl | O | H | $CF_3$ | $CH_3$ | H | $(CH_3)_2NCO$ |
| 8-31 | F | Cl | O | H | $CF_3$ | $CH_3$ | H | $(C_2H_5)_2NCO$ |
| 8-32 | F | Cl | O | H | $CF_3$ | $CH_3$ | H | $C_6H_5CH_2$ |
| 8-33 | F | Cl | O | H | $CF_3$ | $CH_3$ | H | $p\text{-}CH_3OC_6H_4CH_2$ |
| 8-34 | F | Cl | O | H | $CF_3$ | $CH_3$ | H | $p\text{-}ClC_6H_4CH_2$ |
| 8-35 | F | Cl | O | H | $CF_3$ | $CH_3$ | H | $C_6H_5CH_2CH_2$ |
| 8-36 | F | Cl | O | H | $CF_3$ | $CH_3$ | H | $CH_3OOCCH_2$ |
| 8-37 | F | Cl | O | H | $CF_3$ | $CH_3$ | H | $C_2H_5OOCCH_2$ |
| 8-38 | F | Cl | O | H | $CF_3$ | $CH_3$ | H | $(CH_3)_2CHOOCCH_2$ |
| 8-39 | F | Cl | O | H | $CF_3$ | $CH_3$ | H | $^nC_4H_9OOCCH_2$ |
| 8-40 | F | Cl | O | H | $CF_3$ | $CH_3$ | H | $^nC_5H_{11}OOCCH_2$ |
| 8-41 | F | Cl | O | H | $CF_3$ | $CH_3$ | H | $CH_3OOCCH(CH_3)$ |
| 8-42 | F | Cl | O | H | $CF_3$ | $CH_3$ | H | $C_2H_5OOCCH(CH_3)$ |
| 8-43 | F | Cl | O | H | $CF_3$ | $CH_3$ | H | $cC_5H_9OOCCH_2$ |
| 8-44 | F | Cl | O | H | $CF_3$ | $CH_3$ | H | $cC_6H_{11}OOCCH_2$ |
| 8-45 | F | Cl | O | H | $CF_3$ | $CH_3$ | H | $CH_3SO_2$ |
| 8-46 | F | Cl | O | H | $CF_3$ | $CH_3$ | H | $C_2H_5SO_2$ |
| 8-47 | F | Cl | O | H | $CF_3$ | $CH_3$ | H | $(CH_3)_2CHSO_2$ |
| 8-48 | F | Cl | O | H | $CF_3$ | $CH_3$ | H | $ClCH_2SO_2$ |
| 8-49 | F | Cl | O | H | $CF_3$ | $CH_3$ | H | $C_6H_5SO_2$ |
| 8-50 | F | Cl | O | H | $CF_3$ | $CH_3$ | H | $p\text{-}CH_3C_6H_4SO_2$ |
| 8-51 | F | Cl | O | H | $CF_3$ | $CH_3$ | $CH_3$ | $CH_3$ |
| 8-52 | F | Cl | O | H | $CF_3$ | $CH_3$ | $CH_3$ | $C_2H_5$ |
| 8-53 | F | Cl | O | H | $CF_3$ | $CH_3$ | $CH_3$ | $(CH_3)_2CH$ |
| 8-54 | F | Cl | O | H | $CF_3$ | $CH_3$ | $CH_3$ | $(CH_3)_3C$ |
| 8-55 | F | Cl | O | H | $CF_3$ | $CH_3$ | $CH_3$ | $ClCH_2CH_2$ |
| 8-56 | F | Cl | O | H | $CF_3$ | $CH_3$ | $CH_3$ | $CH_3OCH_2$ |
| 8-57 | F | Cl | O | H | $CF_3$ | $CH_3$ | $CH_3$ | $C_2H_5OCH_2$ |
| 8-58 | F | Cl | O | H | $CF_3$ | $CH_3$ | $CH_3$ | $CH_3OCH_2CH_2$ |

TABLE 8-continued

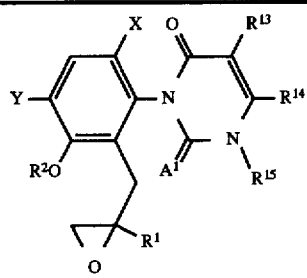

(compound wherein Q is Q-8.)

| Compound No. | X | Y | $A^1$ | $R^{13}$ | $R^{14}$ | $R^{15}$ | $R^1$ | $R^2$ |
|---|---|---|---|---|---|---|---|---|
| 8-59 | F | Cl | O | H | $CF_3$ | $CH_3$ | $CH_3$ | $CH_3OCH_2CH_2OCH_2$ |
| 8-60 | F | Cl | O | H | $CF_3$ | $CH_3$ | $CH_3$ | $CH_3SCH_2$ |
| 8-61 | F | Cl | O | H | $CF_3$ | $CH_3$ | $CH_3$ | $CH_2=CHCH_2$ |
| 8-62 | F | Cl | O | H | $CF_3$ | $CH_3$ | $CH_3$ | $CH_2=CHCH_2CH_2$ |
| 8-63 | F | Cl | O | H | $CF_3$ | $CH_3$ | $CH_3$ | $CH_3-CH=CHCH_2$ |
| 8-64 | F | Cl | O | H | $CF_3$ | $CH_3$ | $CH_3$ | $CH_2=CClCH_2$ |
| 8-65 | F | Cl | O | H | $CF_3$ | $CH_3$ | $CH_3$ | $CCl_2=CHCH_2$ |
| 8-66 | F | Cl | O | H | $CF_3$ | $CH_3$ | $CH_3$ | $CH\equiv CCH_2$ |
| 8-67 | F | Cl | O | H | $CF_3$ | $CH_3$ | $CH_3$ | $CH\equiv CCH(CH_3)$ |
| 8-68 | F | Cl | O | H | $CF_3$ | $CH_3$ | $CH_3$ | $BrC\equiv CCH_2$ |
| 8-69 | F | Cl | O | H | $CF_3$ | $CH_3$ | $CH_3$ | $cC_5H_9$ |
| 8-70 | F | Cl | O | H | $CF_3$ | $CH_3$ | $CH_3$ | $cC_6H_{11}$ |
| 8-71 | F | Cl | O | H | $CF_3$ | $CH_3$ | $CH_3$ | $CH_3CO$ |
| 8-72 | F | Cl | O | H | $CF_3$ | $CH_3$ | $CH_3$ | $C_2H_5CO$ |
| 8-73 | F | Cl | O | H | $CF_3$ | $CH_3$ | $CH_3$ | $(CH_3)_2CHCO$ |
| 8-74 | F | Cl | O | H | $CF_3$ | $CH_3$ | $CH_3$ | $(CH_3)_3CCO$ |
| 8-75 | F | Cl | O | H | $CF_3$ | $CH_3$ | $CH_3$ | $C_6H_5CO$ |
| 8-76 | F | Cl | O | H | $CF_3$ | $CH_3$ | $CH_3$ | $p-CH_3OC_6H_4CO$ |
| 8-77 | F | Cl | O | H | $CF_3$ | $CH_3$ | $CH_3$ | $p-CH_3C_6H_5CO$ |
| 8-78 | F | Cl | O | H | $CF_3$ | $CH_3$ | $CH_3$ | $ClCH_2CO$ |
| 8-79 | F | Cl | O | H | $CF_3$ | $CH_3$ | $CH_3$ | $CH_3NHCO$ |
| 8-80 | F | Cl | O | H | $CF_3$ | $CH_3$ | $CH_3$ | $(CH_3)_2NCO$ |
| 8-81 | F | Cl | O | H | $CF_3$ | $CH_3$ | $CH_3$ | $(C_2H_5)_2NCO$ |
| 8-82 | F | Cl | O | H | $CF_3$ | $CH_3$ | $CH_3$ | $C_6H_5CH_2$ |
| 8-83 | F | Cl | O | H | $CF_3$ | $CH_3$ | $CH_3$ | $p-CH_3OC_6H_4CH_2$ |
| 8-84 | F | Cl | O | H | $CF_3$ | $CH_3$ | $CH_3$ | $p-ClC_6H_4CH_2$ |
| 8-85 | F | Cl | O | H | $CF_3$ | $CH_3$ | $CH_3$ | $C_6H_5CH_2CH_2$ |
| 8-86 | F | Cl | O | H | $CF_3$ | $CH_3$ | $CH_3$ | $CH_3OOCCH_2$ |
| 8-87 | F | Cl | O | H | $CF_3$ | $CH_3$ | $CH_3$ | $C_2H_5OOCCH_2$ |
| 8-88 | F | Cl | O | H | $CF_3$ | $CH_3$ | $CH_3$ | $(CH_3)_2CHOOCCH_2$ |
| 8-89 | F | Cl | O | H | $CF_3$ | $CH_3$ | $CH_3$ | $nC_4H_9OOCCH_2$ |
| 8-90 | F | Cl | O | H | $CF_3$ | $CH_3$ | $CH_3$ | $nC_5H_{11}OOCCH_2$ |
| 8-91 | F | Cl | O | H | $CF_3$ | $CH_3$ | $CH_3$ | $CH_3OOCCH(CH_3)$ |
| 8-92 | F | Cl | O | H | $CF_3$ | $CH_3$ | $CH_3$ | $C_2H_5OOCCH(CH_3)$ |
| 8-93 | F | Cl | O | H | $CF_3$ | $CH_3$ | $CH_3$ | $cC_5H_9OOCCH_2$ |
| 8-94 | F | Cl | O | H | $CF_3$ | $CH_3$ | $CH_3$ | $cC_6H_{11}OOCCH_2$ |
| 8-95 | F | Cl | O | H | $CF_3$ | $CH_3$ | $CH_3$ | $CH_3SO_2$ |
| 8-96 | F | Cl | O | H | $CF_3$ | $CH_3$ | $CH_3$ | $C_2H_5SO_2$ |
| 8-97 | F | Cl | O | H | $CF_3$ | $CH_3$ | $CH_3$ | $(CH_3)_2CHSO_2$ |
| 8-98 | F | Cl | O | H | $CF_3$ | $CH_3$ | $CH_3$ | $ClCH_2SO_2$ |
| 8-99 | F | Cl | O | H | $CF_3$ | $CH_3$ | $CH_3$ | $C_6H_5SO_2$ |
| 8-100 | F | Cl | O | H | $CF_3$ | $CH_3$ | $CH_3$ | $p-CH_3C_6H_4SO_2$ |
| 8-101 | H | Cl | O | H | $CF_3$ | $CH_3$ | H | $CH_3$ |
| 8-102 | H | Cl | O | H | $CF_3$ | $CH_3$ | H | $C_2H_5$ |
| 8-103 | H | Cl | O | H | $CF_3$ | $CH_3$ | H | $(CH_3)_2CH$ |
| 8-104 | H | Cl | O | H | $CF_3$ | $CH_3$ | H | $(CH_3)_3C$ |
| 8-105 | H | Cl | O | H | $CF_3$ | $CH_3$ | H | $ClCH_2CH_2$ |
| 8-106 | H | Cl | O | H | $CF_3$ | $CH_3$ | H | $CH_3OCH_2$ |
| 8-107 | H | Cl | O | H | $CF_3$ | $CH_3$ | H | $C_2H_5OCH_2$ |
| 8-108 | H | Cl | O | H | $CF_3$ | $CH_3$ | H | $CH_3OCH_2CH_2$ |
| 8-109 | H | Cl | O | H | $CF_3$ | $CH_3$ | H | $CH_3OCH_2CH_2OCH_2$ |
| 8-110 | H | Cl | O | H | $CF_3$ | $CH_3$ | H | $CH_3SCH_2$ |
| 8-111 | H | Cl | O | H | $CF_3$ | $CH_3$ | H | $CH_2=CHCH_2$ |
| 8-112 | H | Cl | O | H | $CF_3$ | $CH_3$ | H | $CH_2=CHCH_2CH_2$ |
| 8-113 | H | Cl | O | H | $CF_3$ | $CH_3$ | H | $CH_3-CH=CHCH_2$ |
| 8-114 | H | Cl | O | H | $CF_3$ | $CH_3$ | H | $CH_2=CClCH_2$ |
| 8-115 | H | Cl | O | H | $CF_3$ | $CH_3$ | H | $CCl_2=CHCH_2$ |

TABLE 8-continued

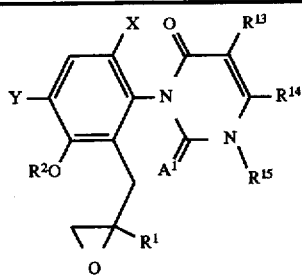

(compound wherein Q is Q-8.)

| Compound No. | X | Y | $A^1$ | $R^{13}$ | $R^{14}$ | $R^{15}$ | $R^1$ | $R^2$ |
|---|---|---|---|---|---|---|---|---|
| 8-116 | H | Cl | O | H | $CF_3$ | $CH_3$ | H | $CH\equiv CCH_2$ |
| 8-117 | H | Cl | O | H | $CF_3$ | $CH_3$ | H | $CH\equiv CCH(CH_3)$ |
| 8-118 | H | Cl | O | H | $CF_3$ | $CH_3$ | H | $BrC\equiv CCH_2$ |
| 8-119 | H | Cl | O | H | $CF_3$ | $CH_3$ | H | $cC_5H_9$ |
| 8-120 | H | Cl | O | H | $CF_3$ | $CH_3$ | H | $cC_6H_{11}$ |
| 8-121 | H | Cl | O | H | $CF_3$ | $CH_3$ | H | $CH_3CO$ |
| 8-122 | H | Cl | O | H | $CF_3$ | $CH_3$ | H | $C_2H_5CO$ |
| 8-123 | H | Cl | O | H | $CF_3$ | $CH_3$ | H | $(CH_3)_2CHCO$ |
| 8-124 | H | Cl | O | H | $CF_3$ | $CH_3$ | H | $(CH_3)_3CCO$ |
| 8-125 | H | Cl | O | H | $CF_3$ | $CH_3$ | H | $C_6H_5CO$ |
| 8-126 | H | Cl | O | H | $CF_3$ | $CH_3$ | H | $p\text{-}CH_3OC_6H_4CO$ |
| 8-127 | H | Cl | O | H | $CF_3$ | $CH_3$ | H | $p\text{-}CH_3C_6H_5CO$ |
| 8-128 | H | Cl | O | H | $CF_3$ | $CH_3$ | H | $ClCH_2CO$ |
| 8-129 | H | Cl | O | H | $CF_3$ | $CH_3$ | H | $CH_3NHCO$ |
| 8-130 | H | Cl | O | H | $CF_3$ | $CH_3$ | H | $(CH_3)_2NCO$ |
| 8-131 | H | Cl | O | H | $CF_3$ | $CH_3$ | H | $(C_2H_5)_2NCO$ |
| 8-132 | H | Cl | O | H | $CF_3$ | $CH_3$ | H | $C_6H_5CH_2$ |
| 8-133 | H | Cl | O | H | $CF_3$ | $CH_3$ | H | $p\text{-}CH_3OC_6H_4CH_2$ |
| 8-134 | H | Cl | O | H | $CF_3$ | $CH_3$ | H | $p\text{-}ClC_6H_4CH_2$ |
| 8-135 | H | Cl | O | H | $CF_3$ | $CH_3$ | H | $C_6H_5CH_2CH_2$ |
| 8-136 | H | Cl | O | H | $CF_3$ | $CH_3$ | H | $CH_3OOCCH_2$ |
| 8-137 | H | Cl | O | H | $CF_3$ | $CH_3$ | H | $C_2H_5OOCCH_2$ |
| 8-138 | H | Cl | O | H | $CF_3$ | $CH_3$ | H | $(CH_3)_2CHOOCCH_2$ |
| 8-139 | H | Cl | O | H | $CF_3$ | $CH_3$ | H | $^nC_4H_9OOCCH_2$ |
| 8-140 | H | Cl | O | H | $CF_3$ | $CH_3$ | H | $^nC_5H_{11}OOCCH_2$ |
| 8-141 | H | Cl | O | H | $CF_3$ | $CH_3$ | H | $CH_3OOCCH(CH_3)$ |
| 8-142 | H | Cl | O | H | $CF_3$ | $CH_3$ | H | $C_2H_5OOCCH(CH_3)$ |
| 8-143 | H | Cl | O | H | $CF_3$ | $CH_3$ | H | $cC_5H_9OOCCH_2$ |
| 8-144 | H | Cl | O | H | $CF_3$ | $CH_3$ | H | $cC_6H_{11}OOCCH_2$ |
| 8-145 | H | Cl | O | H | $CF_3$ | $CH_3$ | H | $CH_3SO_2$ |
| 8-146 | H | Cl | O | H | $CF_3$ | $CH_3$ | H | $C_2H_5SO_2$ |
| 8-147 | H | Cl | O | H | $CF_3$ | $CH_3$ | H | $(CH_3)_2CHSO_2$ |
| 8-148 | H | Cl | O | H | $CF_3$ | $CH_3$ | H | $ClCH_2SO_2$ |
| 8-149 | H | Cl | O | H | $CF_3$ | $CH_3$ | H | $C_6H_5SO_2$ |
| 8-150 | H | Cl | O | H | $CF_3$ | $CH_3$ | H | $p\text{-}CH_3C_6H_4SO_2$ |
| 8-151 | H | Cl | O | H | $CF_3$ | $CH_3$ | $CH_3$ | $CH_3$ |
| 8-152 | H | Cl | O | H | $CF_3$ | $CH_3$ | $CH_3$ | $C_2H_5$ |
| 8-153 | H | Cl | O | H | $CF_3$ | $CH_3$ | $CH_3$ | $(CH_3)_2CH$ |
| 8-154 | H | Cl | O | H | $CF_3$ | $CH_3$ | $CH_3$ | $(CH_3)_3C$ |
| 8-155 | H | Cl | O | H | $CF_3$ | $CH_3$ | $CH_3$ | $ClCH_2CH_2$ |
| 8-156 | H | Cl | O | H | $CF_3$ | $CH_3$ | $CH_3$ | $CH_3OCH_2$ |
| 8-157 | H | Cl | O | H | $CF_3$ | $CH_3$ | $CH_3$ | $C_2H_5OCH_2$ |
| 8-158 | H | Cl | O | H | $CF_3$ | $CH_3$ | $CH_3$ | $CH_3OCH_2CH_2$ |
| 8-159 | H | Cl | O | H | $CF_3$ | $CH_3$ | $CH_3$ | $CH_3OCH_2CH_2OCH_2$ |
| 8-160 | H | Cl | O | H | $CF_3$ | $CH_3$ | $CH_3$ | $CH_3SCH_2$ |
| 8-161 | H | Cl | O | H | $CF_3$ | $CH_3$ | $CH_3$ | $CH_2=CHCH_2$ |
| 8-162 | H | Cl | O | H | $CF_3$ | $CH_3$ | $CH_3$ | $CH_2=CHCH_2CH_2$ |
| 8-163 | H | Cl | O | H | $CF_3$ | $CH_3$ | $CH_3$ | $CH_3-CH=CHCH_2$ |
| 8-164 | H | Cl | O | H | $CF_3$ | $CH_3$ | $CH_3$ | $CH_2=CClCH_2$ |
| 8-165 | H | Cl | O | H | $CF_3$ | $CH_3$ | $CH_3$ | $CCl_2=CHCH_2$ |
| 8-166 | H | Cl | O | H | $CF_3$ | $CH_3$ | $CH_3$ | $CH\equiv CCH_2$ |
| 8-167 | H | Cl | O | H | $CF_3$ | $CH_3$ | $CH_3$ | $CH\equiv CCH(CH_3)$ |
| 8-168 | H | Cl | O | H | $CF_3$ | $CH_3$ | $CH_3$ | $BrC\equiv CCH_2$ |
| 8-169 | H | Cl | O | H | $CF_3$ | $CH_3$ | $CH_3$ | $cC_5H_9$ |
| 8-170 | H | Cl | O | H | $CF_3$ | $CH_3$ | $CH_3$ | $cC_6H_{11}$ |

TABLE 8-continued

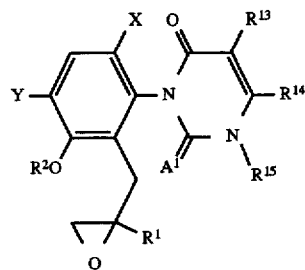

(compound wherein Q is Q-8.)

| Compound No. | X | Y | $A^1$ | $R^{13}$ | $R^{14}$ | $R^{15}$ | $R^1$ | $R^2$ |
|---|---|---|---|---|---|---|---|---|
| 8-171 | H | Cl | O | H | $CF_3$ | $CH_3$ | $CH_3$ | $CH_3CO$ |
| 8-172 | H | Cl | O | H | $CF_3$ | $CH_3$ | $CH_3$ | $C_2H_5CO$ |
| 8-173 | H | Cl | O | H | $CF_3$ | $CH_3$ | $CH_3$ | $(CH_3)_2CHCO$ |
| 8-174 | H | Cl | O | H | $CF_3$ | $CH_3$ | $CH_3$ | $(CH_3)_3CCO$ |
| 8-175 | H | Cl | O | H | $CF_3$ | $CH_3$ | $CH_3$ | $C_6H_5CO$ |
| 8-176 | H | Cl | O | H | $CF_3$ | $CH_3$ | $CH_3$ | $p\text{-}CH_3OC_6H_4CO$ |
| 8-177 | H | Cl | O | H | $CF_3$ | $CH_3$ | $CH_3$ | $p\text{-}CH_3C_6H_5CO$ |
| 8-178 | H | Cl | O | H | $CF_3$ | $CH_3$ | $CH_3$ | $ClCH_2CO$ |
| 8-179 | H | Cl | O | H | $CF_3$ | $CH_3$ | $CH_3$ | $CH_3NHCO$ |
| 8-180 | H | Cl | O | H | $CF_3$ | $CH_3$ | $CH_3$ | $(CH_3)_2NCO$ |
| 8-181 | H | Cl | O | H | $CF_3$ | $CH_3$ | $CH_3$ | $(C_2H_5)_2NCO$ |
| 8-182 | H | Cl | O | H | $CF_3$ | $CH_3$ | $CH_3$ | $C_6H_5CH_2$ |
| 8-183 | H | Cl | O | H | $CF_3$ | $CH_3$ | $CH_3$ | $p\text{-}CH_3OC_6H_4CH_2$ |
| 8-184 | H | Cl | O | H | $CF_3$ | $CH_3$ | $CH_3$ | $p\text{-}ClC_6H_4CH_2$ |
| 8-185 | H | Cl | O | H | $CF_3$ | $CH_3$ | $CH_3$ | $C_6H_5CH_2CH_2$ |
| 8-186 | H | Cl | O | H | $CF_3$ | $CH_3$ | $CH_3$ | $CH_3OOCCH_2$ |
| 8-187 | H | Cl | O | H | $CF_3$ | $CH_3$ | $CH_3$ | $C_2H_5OOCCH_2$ |
| 8-188 | H | Cl | O | H | $CF_3$ | $CH_3$ | $CH_3$ | $(CH_3)_2CHOOCCH_2$ |
| 8-189 | H | Cl | O | H | $CF_3$ | $CH_3$ | $CH_3$ | $^nC_4H_9OOCCH_2$ |
| 8-190 | H | Cl | O | H | $CF_3$ | $CH_3$ | $CH_3$ | $^nC_5H_{11}OOCCH_2$ |
| 8-191 | H | Cl | O | H | $CF_3$ | $CH_3$ | $CH_3$ | $CH_3OOCCH(CH_3)$ |
| 8-192 | H | Cl | O | H | $CF_3$ | $CH_3$ | $CH_3$ | $C_2H_5OOCCH(CH_3)$ |
| 8-193 | H | Cl | O | H | $CF_3$ | $CH_3$ | $CH_3$ | $cC_5H_9OOCCH_2$ |
| 8-194 | H | Cl | O | H | $CF_3$ | $CH_3$ | $CH_3$ | $cC_6H_{11}OOCCH_2$ |
| 8-195 | H | Cl | O | H | $CF_3$ | $CH_3$ | $CH_3$ | $CH_3SO_2$ |
| 8-196 | H | Cl | O | H | $CF_3$ | $CH_3$ | $CH_3$ | $C_2H_5SO_2$ |
| 8-197 | H | Cl | O | H | $CF_3$ | $CH_3$ | $CH_3$ | $(CH_3)_2CHSO_2$ |
| 8-198 | H | Cl | O | H | $CF_3$ | $CH_3$ | $CH_3$ | $ClCH_2SO_2$ |
| 8-199 | H | Cl | O | H | $CF_3$ | $CH_3$ | $CH_3$ | $C_6H_5SO_2$ |
| 8-200 | H | Cl | O | H | $CF_3$ | $CH_3$ | $CH_3$ | $p\text{-}CH_3C_6H_4SO_2$ |
| 8-201 | F | Br | O | H | $CF_3$ | $CH_3$ | H | $(CH_3)_2CH$ |
| 8-202 | F | F | O | H | $CF_3$ | $CH_3$ | H | $CH\equiv CCH_2$ |
| 8-203 | Cl | Cl | O | H | $CF_3$ | $CH_3$ | $CH_3$ | $CH\equiv CCH(CH_3)$ |
| 8-204 | F | Cl | S | H | $CF_3$ | $CH_3$ | $CH_3$ | $CH_3CO$ |
| 8-205 | F | Cl | O | H | $CF_3$ | $NH_2$ | $CH_3$ | $C_6H_5CO$ |
| 8-206 | F | Cl | S | H | $CF_3$ | $NH_2$ | H | $CH_3OCH_2$ |
| 8-207 | F | Cl | O | H | $CF_3CF_2$ | $CH_3$ | $CH_3$ | $CH_2=CHCH_2$ |
| 8-208 | F | Cl | O | Cl | $CF_3$ | $CH_3$ | $CH_3$ | $CH_3OOCCH_2$ |

TABLE 9

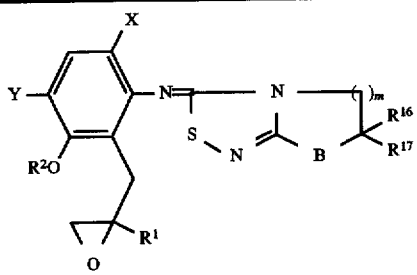

(compound wherein Q is Q-9.)

| Compound No. | X | Y | B | R15 | R17 | m | R1 | R2 |
|---|---|---|---|---|---|---|---|---|
| 9-1 | F | Cl | $CH_2$ | $CH_3$ | $CH_3$ | 1 | H | $(CH_3)_2CH$ |
| 9-2 | F | Cl | $CH_2$ | $CH_3$ | $CH_3$ | 1 | H | $ClCH_2CH_2$ |
| 9-3 | F | Cl | $CH_2$ | $CH_3$ | $CH_3$ | 1 | H | $CH_3OCH_2$ |
| 9-4 | F | Cl | $CH_2$ | $CH_3$ | $CH_3$ | 1 | H | $CH_3OCH_2CH_2OCH_2$ |
| 9-5 | F | Cl | $CH_2$ | $CH_3$ | $CH_3$ | 1 | H | $CH_3SCH_2$ |
| 9-6 | F | Cl | $CH_2$ | $CH_3$ | $CH_3$ | 1 | H | $CH_2=CHCH_2$ |
| 9-7 | F | Cl | $CH_2$ | $CH_3$ | $CH_3$ | 1 | H | $CH_2=CClCH_2$ |
| 9-8 | F | Cl | $CH_2$ | $CH_3$ | $CH_3$ | 1 | H | $CH\equiv CCH_2$ |
| 9-9 | F | Cl | $CH_2$ | $CH_3$ | $CH_3$ | 1 | H | $CH\equiv CCH(CH_3)$ |
| 9-10 | F | Cl | $CH_2$ | $CH_3$ | $CH_3$ | 1 | H | $cC_5H_9$ |
| 9-11 | F | Cl | $CH_2$ | $CH_3$ | $CH_3$ | 1 | H | $CH_3CO$ |
| 9-12 | F | Cl | $CH_2$ | $CH_3$ | $CH_3$ | 1 | H | $CH_3NHCO$ |
| 9-13 | F | Cl | $CH_2$ | $CH_3$ | $CH_3$ | 1 | H | $C_6H_5CO$ |
| 9-14 | F | Cl | $CH_2$ | $CH_3$ | $CH_3$ | 1 | H | $C_6H_5CH_2$ |
| 9-15 | F | Cl | $CH_2$ | $CH_3$ | $CH_3$ | 1 | H | $CH_3OOCCH_2$ |
| 9-16 | F | Cl | $CH_2$ | $CH_3$ | $CH_3$ | 1 | H | $CH_3SO_2$ |
| 9-17 | F | Cl | $CH_2$ | $CH_3$ | $CH_3$ | 1 | $CH_3$ | $(CH_3)_2CH$ |
| 9-18 | F | Cl | $CH_2$ | $CH_3$ | $CH_3$ | 1 | $CH_3$ | $ClCH_2CH_2$ |
| 9-19 | F | Cl | $CH_2$ | $CH_3$ | $CH_3$ | 1 | $CH_3$ | $CH_3OCH_2$ |
| 9-20 | F | Cl | $CH_2$ | $CH_3$ | $CH_3$ | 1 | $CH_3$ | $CH_3OCH_2CH_2OCH_2$ |
| 9-21 | F | Cl | $CH_2$ | $CH_3$ | $CH_3$ | 1 | $CH_3$ | $CH_3SCH_2$ |
| 9-22 | F | Cl | $CH_2$ | $CH_3$ | $CH_3$ | 1 | $CH_3$ | $CH_2=CHCH_2$ |
| 9-23 | F | Cl | $CH_2$ | $CH_3$ | $CH_3$ | 1 | $CH_3$ | $CH_2=CClCH_2$ |
| 9-24 | F | Cl | $CH_2$ | $CH_3$ | $CH_3$ | 1 | $CH_3$ | $CH\equiv CCH_2$ |
| 9-25 | F | Cl | $CH_2$ | $CH_3$ | $CH_3$ | 1 | $CH_3$ | $CH\equiv CCH(CH_3)$ |
| 9-26 | F | Cl | $CH_2$ | $CH_3$ | $CH_3$ | 1 | $CH_3$ | $cC_5H_9$ |
| 9-27 | F | Cl | $CH_2$ | $CH_3$ | $CH_3$ | 1 | $CH_3$ | $CH_3CO$ |
| 9-28 | F | Cl | $CH_2$ | $CH_3$ | $CH_3$ | 1 | $CH_3$ | $CH_3NHCO$ |
| 9-29 | F | Cl | $CH_2$ | $CH_3$ | $CH_3$ | 1 | $CH_3$ | $C_6H_5CO$ |
| 9-30 | F | Cl | $CH_2$ | $CH_3$ | $CH_3$ | 1 | $CH_3$ | $C_6H_5CH_2$ |
| 9-31 | F | Cl | $CH_2$ | $CH_3$ | $CH_3$ | 1 | $CH_3$ | $CH_3OOCCH_2$ |
| 9-32 | F | Cl | $CH_2$ | $CH_3$ | $CH_3$ | 1 | $CH_3$ | $CH_3SO_2$ |
| 9-33 | H | Cl | $CH_2$ | $CH_3$ | $CH_3$ | 1 | H | $(CH_3)_2CH$ |
| 9-34 | H | Cl | $CH_2$ | $CH_3$ | $CH_3$ | 1 | H | $ClCH_2CH_2$ |
| 9-35 | H | Cl | $CH_2$ | $CH_3$ | $CH_3$ | 1 | H | $CH_3OCH_2$ |
| 9-36 | H | Cl | $CH_2$ | $CH_3$ | $CH_3$ | 1 | H | $CH_3OCH_2CH_2OCH_2$ |
| 9-37 | H | Cl | $CH_2$ | $CH_3$ | $CH_3$ | 1 | H | $CH_3SCH_2$ |
| 9-38 | H | Cl | $CH_2$ | $CH_3$ | $CH_3$ | 1 | H | $CH_2=CHCH_2$ |
| 9-39 | H | Cl | $CH_2$ | $CH_3$ | $CH_3$ | 1 | H | $CH_2=CClCH_2$ |
| 9-40 | H | Cl | $CH_2$ | $CH_3$ | $CH_3$ | 1 | H | $CH\equiv CCH_2$ |
| 9-41 | H | Cl | $CH_2$ | $CH_3$ | $CH_3$ | 1 | H | $CH\equiv CCH(CH_3)$ |
| 9-42 | H | Cl | $CH_2$ | $CH_3$ | $CH_3$ | 1 | H | $cC_5H_9$ |
| 9-43 | H | Cl | $CH_2$ | $CH_3$ | $CH_3$ | 1 | H | $CH_3CO$ |
| 9-44 | H | Cl | $CH_2$ | $CH_3$ | $CH_3$ | 1 | H | $CH_3NHCO$ |
| 9-45 | H | Cl | $CH_2$ | $CH_3$ | $CH_3$ | 1 | H | $C_6H_5CO$ |
| 9-46 | H | Cl | $CH_2$ | $CH_3$ | $CH_3$ | 1 | H | $C_6H_5CH_2$ |
| 9-47 | H | Cl | $CH_2$ | $CH_3$ | $CH_3$ | 1 | H | $CH_3OOCCH_2$ |
| 9-48 | H | Cl | $CH_2$ | $CH_3$ | $CH_3$ | 1 | H | $CH_3SO_2$ |
| 9-49 | H | Cl | $CH_2$ | $CH_3$ | $CH_3$ | 1 | $CH_3$ | $(CH_3)_2CH$ |
| 9-50 | H | Cl | $CH_2$ | $CH_3$ | $CH_3$ | 1 | $CH_3$ | $ClCH_2CH_2$ |
| 9-51 | H | Cl | $CH_2$ | $CH_3$ | $CH_3$ | 1 | $CH_3$ | $CH_3OCH_2$ |
| 9-52 | H | Cl | $CH_2$ | $CH_3$ | $CH_3$ | 1 | $CH_3$ | $CH_3OCH_2CH_2OCH_2$ |
| 9-53 | H | Cl | $CH_2$ | $CH_3$ | $CH_3$ | 1 | $CH_3$ | $CH_3SCH_2$ |
| 9-54 | H | Cl | $CH_2$ | $CH_3$ | $CH_3$ | 1 | $CH_3$ | $CH_2=CHCH_2$ |
| 9-55 | H | Cl | $CH_2$ | $CH_3$ | $CH_3$ | 1 | $CH_3$ | $CH_2=CClCH_2$ |

TABLE 9-continued

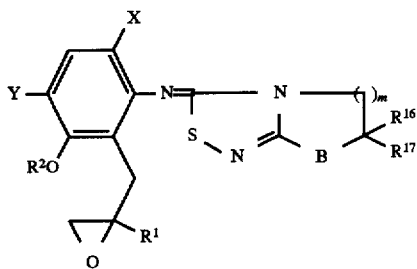

(compound wherein Q is Q-9.)

| Compound No. | X | Y | B | R15 | R17 | m | R1 | R2 |
|---|---|---|---|---|---|---|---|---|
| 9-56 | H | Cl | $CH_2$ | $CH_3$ | $CH_3$ | 1 | $CH_3$ | $CH\equiv CCH_2$ |
| 9-57 | H | Cl | $CH_2$ | $CH_3$ | $CH_3$ | 1 | $CH_3$ | $CH\equiv CCH(CH_3)$ |
| 9-58 | H | Cl | $CH_2$ | $CH_3$ | $CH_3$ | 1 | $CH_3$ | $cC_5H_9$ |
| 9-59 | H | Cl | $CH_2$ | $CH_3$ | $CH_3$ | 1 | $CH_3$ | $CH_3CO$ |
| 9-60 | H | Cl | $CH_2$ | $CH_3$ | $CH_3$ | 1 | $CH_3$ | $CH_3NHCO$ |
| 9-61 | H | Cl | $CH_2$ | $CH_3$ | $CH_3$ | 1 | $CH_3$ | $C_6H_5CO$ |
| 9-62 | H | Cl | $CH_2$ | $CH_3$ | $CH_3$ | 1 | $CH_3$ | $C_6H_5CH_2$ |
| 9-63 | H | Cl | $CH_2$ | $CH_3$ | $CH_3$ | 1 | $CH_3$ | $CH_3OOCCH_2$ |
| 9-64 | H | Cl | $CH_2$ | $CH_3$ | $CH_3$ | 1 | $CH_3$ | $CH_3SO_2$ |

TABLE 10

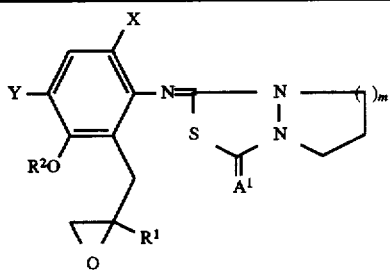

(compound wherein Q is Q-10.)

| Compound No. | X | Y | A1 | m | R1 | R2 |
|---|---|---|---|---|---|---|
| 10-1 | F | Cl | O | 2 | H | $(CH_3)_2CH$ |
| 10-2 | F | Cl | O | 2 | H | $ClCH_2CH_2$ |
| 10-3 | F | Cl | O | 2 | H | $CH_3OCH_2$ |
| 10-4 | F | Cl | O | 2 | H | $CH_3OCH_2CH_2OCH_2$ |
| 10-5 | F | Cl | O | 2 | H | $CH_3SCH_2$ |
| 10-6 | F | Cl | O | 2 | H | $CH_2=CHCH_2$ |
| 10-7 | F | Cl | O | 2 | H | $CH_2=CClCH_2$ |
| 10-8 | F | Cl | O | 2 | H | $CH\equiv CCH_2$ |
| 10-9 | F | Cl | O | 2 | H | $CH\equiv CCH(CH_3)$ |
| 10-10 | F | Cl | O | 2 | H | $cC_5H_9$ |
| 10-11 | F | Cl | O | 2 | H | $CH_3CO$ |
| 10-12 | F | Cl | O | 2 | H | $CH_3NHCO$ |
| 10-13 | F | Cl | O | 2 | H | $C_6H_5CO$ |
| 10-14 | F | Cl | O | 2 | H | $C_6H_5CH_2$ |
| 10-15 | F | Cl | O | 2 | H | $CH_3OOCCH_2$ |
| 10-16 | F | Cl | O | 2 | H | $CH_3SO_2$ |
| 10-17 | F | Cl | O | 2 | $CH_3$ | $(CH_3)_2CH$ |
| 10-18 | F | Cl | O | 2 | $CH_3$ | $ClCH_2CH_2$ |
| 10-19 | F | Cl | O | 2 | $CH_3$ | $CH_3OCH_2$ |
| 10-20 | F | Cl | O | 2 | $CH_3$ | $CH_3OCH_2CH_2OCH_2$ |
| 10-21 | F | Cl | O | 2 | $CH_3$ | $CH_3SCH_2$ |
| 10-22 | F | Cl | O | 2 | $CH_3$ | $CH_2=CHCH_2$ |
| 10-23 | F | Cl | O | 2 | $CH_3$ | $CH_2=CClCH_2$ |
| 10-24 | F | Cl | O | 2 | $CH_3$ | $CH\equiv CCH_2$ |

TABLE 10-continued

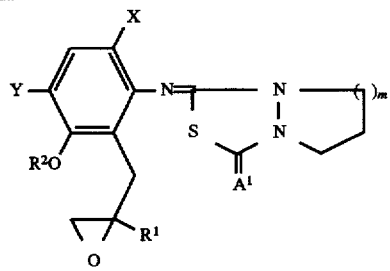

(compound wherein Q is Q-10.)

| Compound No. | X | Y | A1 | m | R1 | R2 |
|---|---|---|---|---|---|---|
| 10-25 | F | Cl | O | 2 | $CH_3$ | $CH\equiv CCH(CH_3)$ |
| 10-26 | F | Cl | O | 2 | $CH_3$ | $cC_5H_9$ |
| 10-27 | F | Cl | O | 2 | $CH_3$ | $CH_3CO$ |
| 10-28 | F | Cl | O | 2 | $CH_3$ | $CH_3NHCO$ |
| 10-29 | F | Cl | O | 2 | $CH_3$ | $C_6H_5CO$ |
| 10-30 | F | Cl | O | 2 | $CH_3$ | $C_6H_5CH_2$ |
| 10-31 | F | Cl | O | 2 | $CH_3$ | $CH_3OOCCH_2$ |
| 10-32 | F | Cl | O | 2 | $CH_3$ | $CH_3SO_2$ |
| 10-33 | H | Cl | O | 2 | H | $(CH_3)_2CH$ |
| 10-34 | H | Cl | O | 2 | H | $ClCH_2CH_2$ |
| 10-35 | F | Cl | O | 2 | H | $CH_3OCH_2$ |
| 10-36 | H | Cl | O | 2 | H | $CH_3OCH_2CH_2OCH_2$ |
| 10-37 | H | Cl | O | 2 | H | $CH_3SCH_2$ |
| 10-38 | H | Cl | O | 2 | H | $CH_2=CHCH_2$ |
| 10-39 | H | Cl | O | 2 | H | $CH_2=CClCH_2$ |
| 10-40 | H | Cl | O | 2 | H | $CH\equiv CCH_2$ |
| 10-41 | H | Cl | O | 2 | H | $CH\equiv CCH(CH_3)$ |
| 10-42 | H | Cl | O | 2 | H | $cC_5H_9$ |
| 10-43 | H | Cl | O | 2 | H | $CH_3CO$ |
| 10-44 | H | Cl | O | 2 | H | $CH_3NHCO$ |
| 10-45 | H | Cl | O | 2 | H | $C_6H_5CO$ |
| 10-46 | H | Cl | O | 2 | H | $C_6H_5CH_2$ |
| 10-47 | H | Cl | O | 2 | H | $CH_3OOCCH_2$ |
| 10-48 | H | Cl | O | 2 | H | $CH_3SO_2$ |

TABLE 10-continued

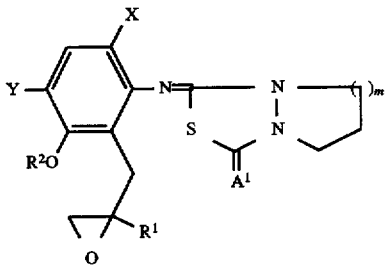

(compound wherein Q is Q-10.)

| Compound No. | X | Y | A¹ | m | R¹ | R² |
|---|---|---|---|---|---|---|
| 10-49 | H | Cl | O | 2 | CH₃ | (CH₃)₂CH |
| 10-50 | H | Cl | O | 2 | CH₃ | ClCH₂CH₂ |
| 10-51 | H | Cl | O | 2 | CH₃ | CH₃OCH₂ |
| 10-52 | H | Cl | O | 2 | CH₃ | CH₃OCH₂CH₂OCH₂ |
| 10-53 | H | Cl | O | 2 | CH₃ | CH₃SCH₂ |
| 10-54 | H | Cl | O | 2 | CH₃ | CH₂=CHCH₂ |
| 10-55 | H | Cl | O | 2 | CH₃ | CH₂=CClCH₂ |
| 10-56 | H | Cl | O | 2 | CH₃ | CH≡CCH₂ |
| 10-57 | H | Cl | O | 2 | CH₃ | CH≡CCH(CH₃) |
| 10-58 | H | Cl | O | 2 | CH₃ | cC₅H₉ |
| 10-59 | H | Cl | O | 2 | CH₃ | CH₃CO |
| 10-60 | H | Cl | O | 2 | CH₃ | CH₃NHCO |
| 10-61 | H | Cl | O | 2 | CH₃ | C₆H₅CO |
| 10-62 | H | Cl | O | 2 | CH₃ | C₆H₅CH₂ |
| 10-63 | H | Cl | O | 2 | CH₃ | CH₃OOCCH₂ |
| 10-64 | H | Cl | O | 2 | CH₃ | CH₃SO₂ |
| 10-65 | F | Br | O | 2 | CH₃ | (CH₃)₂CH |
| 10-66 | F | F | O | 2 | CH₃ | (CH₃)₂CH |
| 10-67 | Cl | Cl | O | 2 | CH₃ | (CH₃)₂CH |
| 10-68 | F | Cl | O | 1 | CH₃ | (CH₃)₂CH |

TABLE 11

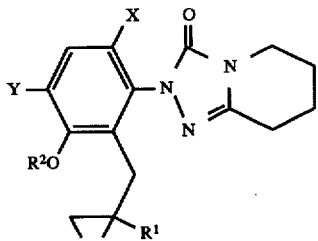

(compound wherein Q is Q-11.)

| Compound No. | X | Y | R¹ | R² |
|---|---|---|---|---|
| 11-1 | F | Cl | H | (CH₃)₂CH |
| 11-2 | F | Cl | H | ClCH₂CH₂ |
| 11-3 | F | Cl | H | CH₃OCH₂ |
| 11-4 | F | Cl | H | CH₃OCH₂CH₂OCH₂ |
| 11-5 | F | Cl | H | CH₃SCH₂ |
| 11-6 | F | Cl | H | CH₂=CHCH₂ |
| 11-7 | F | Cl | H | CH₂=CClCH₂ |
| 11-8 | F | Cl | H | CH≡CCH₂ |
| 11-9 | F | Cl | H | CH≡CCH(CH₃) |
| 11-10 | F | Cl | H | cC₅H₉ |
| 11-11 | F | Cl | H | CH₃CO |
| 11-12 | F | Cl | H | CH₃NHCO |
| 11-13 | F | Cl | H | C₆H₅CO |
| 11-14 | F | Cl | H | C₆H₅CH₂ |
| 11-15 | F | Cl | H | CH₃OOCCH₂ |

TABLE 11-continued

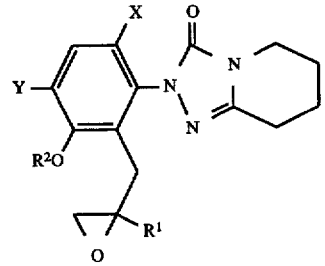

(compound wherein Q is Q-11.)

| Compound No. | X | Y | R¹ | R² |
|---|---|---|---|---|
| 11-16 | F | Cl | H | CH₃SO₂ |
| 11-17 | F | Cl | CH₃ | (CH₃)₂CH |
| 11-18 | F | Cl | CH₃ | ClCH₂CH₂ |
| 11-19 | F | Cl | CH₃ | CH₃OCH₂ |
| 11-20 | F | Cl | CH₃ | CH₃OCH₂CH₂OCH₂ |
| 11-21 | F | Cl | CH₃ | CH₃SCH₂ |
| 11-22 | F | Cl | CH₃ | CH₂=CHCH₂ |
| 11-23 | F | Cl | CH₃ | CH₂=CClCH₂ |
| 11-24 | F | Cl | CH₃ | CH≡CCH₂ |
| 11-25 | F | Cl | CH₃ | CH≡CCH(CH₃) |
| 11-26 | F | Cl | CH₃ | cC₅H₉ |
| 11-27 | F | Cl | CH₃ | CH₃CO |
| 11-28 | F | Cl | CH₃ | CH₃NHCO |
| 11-29 | F | Cl | CH₃ | C₆H₅CO |
| 11-30 | F | Cl | CH₃ | C₆H₅CH₂ |
| 11-31 | F | Cl | CH₃ | CH₃OOCCH₂ |
| 11-32 | F | Cl | CH₃ | CH₃SO₂ |
| 11-33 | H | Cl | H | (CH₃)₂CH |
| 11-34 | H | Cl | H | ClCH₂CH₂ |
| 11-35 | H | Cl | H | CH₃OCH₂ |
| 11-36 | H | Cl | H | CH₃OCH₂CH₂OCH₂ |
| 11-37 | H | Cl | H | CH₃SCH₂ |
| 11-38 | H | Cl | H | CH₂=CHCH₂ |
| 11-39 | H | Cl | H | CH₂=CClCH₂ |
| 11-40 | H | Cl | H | CH≡CCH₂ |
| 11-41 | H | Cl | H | CH≡CCH(CH₃) |
| 11-42 | H | Cl | H | cC₅H₉ |
| 11-43 | H | Cl | H | CH₃CO |
| 11-44 | H | Cl | H | CH₃NHCO |
| 11-45 | H | Cl | H | C₆H₅CO |
| 11-46 | H | Cl | H | C₆H₅CH₂ |
| 11-47 | H | Cl | H | CH₃OOCCH₂ |
| 11-48 | H | Cl | H | CH₃SO₂ |
| 11-49 | H | Cl | CH₃ | (CH₃)₂CH |
| 11-50 | H | Cl | CH₃ | ClCH₂CH₂ |
| 11-51 | H | Cl | CH₃ | CH₃OCH₂ |
| 11-52 | H | Cl | CH₃ | CH₃OCH₂CH₂OCH₂ |
| 11-53 | H | Cl | CH₃ | CH₃SCH₂ |
| 11-54 | H | Cl | CH₃ | CH₂=CHCH₂ |
| 11-55 | H | Cl | CH₃ | CH₂=CClCH₂ |
| 11-56 | H | Cl | CH₃ | CH≡CCH₂ |
| 11-57 | H | Cl | CH₃ | CH≡CCH(CH₃) |
| 11-58 | H | Cl | CH₃ | cC₅H₉ |
| 11-59 | H | Cl | CH₃ | CH₃CO |
| 11-60 | H | Cl | CH₃ | CH₃NHCO |
| 11-61 | H | Cl | CH₃ | C₆H₅CO |
| 11-62 | H | Cl | CH₃ | C₆H₅CH₂ |
| 11-63 | H | Cl | CH₃ | CH₃OOCCH₂ |
| 11-64 | H | Cl | CH₃ | CH₃SO₂ |
| 11-65 | F | Br | H | (CH₃)₂CH |
| 11-66 | F | F | H | (CH₃)₂CH |
| 11-67 | Cl | Cl | H | (CH₃)₂CH |

TABLE 12

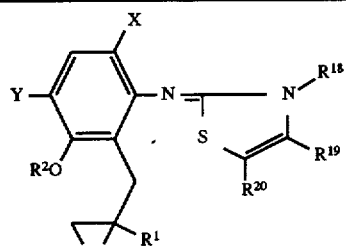

(compound wherein Q is Q-12.)

| Compound No. | X | Y | R¹ | R² | R¹⁸ | R¹⁹ | R²⁰ |
|---|---|---|---|---|---|---|---|
| 12-1 | F | Cl | H | $(CH_3)_2CH$ | $CH_3$ | $CH_3$ | H |
| 12-2 | F | Cl | H | $CH_3OCH_2$ | $CH_3$ | $CF_3$ | H |
| 12-3 | F | Cl | H | $CH\equiv CCH_2$ | $CH_2CH=CH_2$ | $CH_3$ | H |
| 12-4 | F | Cl | H | $CH_3CO$ | $CH_3$ | $CF_3$ | H |
| 12-5 | F | Cl | H | $CH_3OOCCH_2$ | $CH_3$ | $CH_3$ | H |
| 12-6 | F | Cl | $CH_3$ | $CH_3$ | $CH_2CH=CH_2$ | $CH_3$ | H |
| 12-7 | H | Cl | H | $(CH_3)_2CH$ | $CH_3$ | $CF_3$ | H |
| 12-8 | H | Cl | $CH_3$ | $CH_3CO$ | $CH_3$ | $CF_3$ | H |

TABLE 13

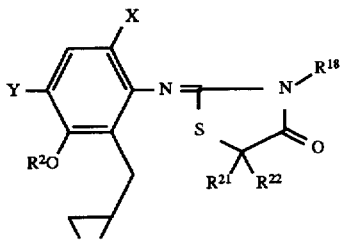

(compound wherein Q is Q-13.)

| Compound No. | X | Y | R¹ | R² | R¹⁸ | R²¹ | R²² |
|---|---|---|---|---|---|---|---|
| 13-1 | F | Cl | H | $(CH_3)_2CH$ | $CH_3$ | H | H |
| 13-2 | F | Cl | H | $CH_3CO$ | $CH_3$ | H | H |
| 13-3 | F | Cl | H | $CH_3OCH_2$ | $CH_2CH=CH_2$ | H | $CH_3$ |
| 13-4 | F | Cl | H | $CH\equiv CCH_2$ | $CH_3$ | $CH_3$ | $CH_3$ |
| 13-5 | F | Cl | H | $CH_3OOCCH_2$ | $CH_3$ | H | H |
| 13-6 | F | Cl | $CH_3$ | $CH_3$ | $CH_3$ | H | H |
| 13-7 | H | Cl | $CH_3$ | $CH_3CO$ | $CH_3$ | H | Cl |
| 13-8 | H | Cl | H | $CH_3OCH_2$ | $CH_2CH=CH_2$ | H | H |

The compound [2], which is a starting compound used in the production of the present compounds, can be produced by reacting a phenol compound of the formula:

[7]

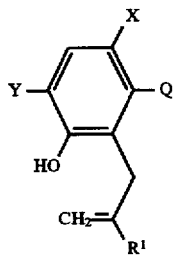

wherein X, Y, Q and R¹ are each as defined above, with a compound of the formula:

$$R^2-D^1 \qquad [8]$$

wherein R² is as defined above; and D¹ is chlorine, bromine, iodine, $C_1-C_4$ alkylsulfonyloxy such as methanesulfonyloxy, or benzenesulfonyloxy which may be optionally substituted with at least one $C_1-C_4$ alkyl group, $C_1-C_4$ alkoxy group or halogen atom, such as p-toluenesulfonyloxy or benzenesulfonyloxy.

The reaction is usually effected in a solvent in the presence of a base. The reaction temperature is usually in the range of <20° to the refluxing temperature of the solvent. The reaction time is usually in the range of a moment to 48 hours. The amounts of the reagents to be used in the reaction are usually 1 to 10 moles of the compound [8] and usually 1 mole to an excess of the base, per mole of the compound [7].

Examples of the solvent which can be used include aliphatic hydrocarbons such as petroleum ether and hexane; aromatic hydrocarbons such as toluene and xylene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethyl-formamide and acetamide; sulfur compounds such as dimethylsulfoxide and sulfolane; and mixtures thereof.

Examples of the base which can be used include inorganic bases such as potassium carbonate, sodium hydroxide and potassium hydroxide; metal hydrides such as sodium hydride and potassium hydride; organic bases such as triethylamine, diisopropylethylamine, pyridine and 4-dimethylaminopyridine; and mixtures thereof.

After completion of the reaction, the reaction mixture is poured into water, and the precipitated crystals are collected by filtration, or the reaction mixture is subjected to ordinary post-treatments such as extraction with an organic solvent and concentration, followed by, if necessary, subsequent purification such as chromatography or recrystallization. Thus, the desired compounds can be isolated.

The compound [3] can be produced by reacting the compound [7] with an epoxidizing agent.

The reaction is usually effected in a solvent. The reaction temperature is usually in the range of −20° to 150° C., preferably 0° to 60° C. The reaction time is usually in the range of a moment to 48 hours. The amount of the epoxidizing agent to be used in the reaction is usually 1 to 5 moles per mole of the compound [7].

Examples of the solvent which can be used include aliphatic hydrocarbons such as petroleum ether and hexane; fatty acids such as formic acid and acetic acid; and halogenated hydrocarbons such as methylene chloride, chloroform and 1,2-dichloroethane. Examples of the epoxidizing agent include peracids such as perbenzoic acid, m-chloroperbenzoic acid, peracetic acid and trifluoroperacetic acid.

After completion of the reaction, the reaction mixture is treated, if necessary, with a reducing agent such as aqueous sodium thiosulfate solution or aqueous sodium sulfite solution, followed by ordinary post-treatments such as extraction with an organic solvent and concentration, and if necessary, subsequent purification such as recrystallization. Thus, the compound [3] can be isolated.

The compound [7] can be produced by the method described in, for example, U.S. Pat. No. 4,881,967 or JP-A 156787/1988, or by reacting a compound of the formula:

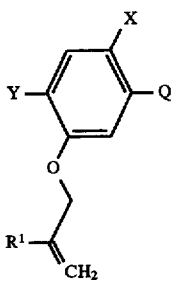

[9]

wherein X, Y, R¹ and Q are each as defined above, without any solvent or in a solvent, usually at 20° to 300° C., preferably 100° to 250° C., usually for 0.5 to 48 hours.

Examples of the solvent which can be used include aliphatic hydrocarbons such as petroleum ether and hexane; aromatic hydrocarbons such as toluene, xylene and m-isobutylbenzene; halogenated hydrocarbons such as chloroform, 1,2-dichloroethane, chlorobenzene and o-dichlorobenzene; ethers such as diethyl ether, diisopropyl ether, 1,4-dioxane, tetrahydrofuran and ethylene glycol dimethyl ether; ketones such as acetone, methyl isobutyl ketone and cyclohexanone; fatty acids such as formic acid and acetic acid; alcohols such as methanol, ethanol and ethylene glycol; esters such as ethyl acetate and diethyl carbonate; nitro compounds such as nitroethane and nitrobenzene; nitriles such as acetonitrile and isobutyronitrile; tertiary amines such as pyridine, triethylamine, N,N-dimethylaniline, N,N-diethylaniline and N-methylmorpholine; acid amides such as formamide, N,N-dimethylformamide and acetamide; sulfur compounds such as dimethylsulfoxide and sulfolane; water; and mixtures thereof.

After completion of the reaction, the reaction mixture is poured into water, and the precipitated crystals are collected by filtration, or the reaction mixture is subjected to ordinary post-treatments such as extraction with an organic solvent and concentration, followed by, if necessary, subsequent purification such as chromatography, distillation or recrystallization. Thus, the desired compound can be isolated.

The compound [9] can be produced according to the method described in, for example, JP-A 41466/1988, JP-A 156787/1988, JP-A 264489/1988, JP-A 181283/1987 or EP-517181-A, or as disclosed in any reference cited in these specifications and publications.

The present compounds have excellent herbicidal activity, and some of them exhibit excellent selectivity between crop plants and unfavorable weeds. In particular, the present compounds have herbicidal activity against various unfavorable weeds as recited below, which may cause trouble in the foliar treatment and soil treatment on upland fields. Polygonaceae:

wild buckwheat (Polygonum convolvulus), pale smartweed (Polygonum lapathifolium), Pennsylvania smartweed (Polygonum pensylvanicum), ladysthumb (Polygonum persicaria), curly dock (Rumex crispus), broadleaf dock (Rumex obtusifolius), Japanese knotweed (Polygonum cuspidatum) Portulacaceae:

common purslane (Portulaca oleracea) Caryophyllaceae:

common chickweed (Stellaria media) Chenopodiaceae:

common lambsquarters (Chenopodium album), kochia (Kochia scoparia) Amaranthaceae:

redroot pigweed (Amaranthus retroflexus), smooth pigweed (Amaranthus hybridus) Crusiferae:

wild radish (Raphanus raphanistrum), wild mustard (Sinapis arvensis), shepherdspurse (Capsella bursa-pastoris) Leguminosae:

hemp sesbania (Sesbania exaltata), sicklepod (Cassia obtusifolia), Florida beggarweed (Desmodium tortuosum), white clover (Trifolium repens) Malvaceae:

velvetleaf (Abutilon theophrasti), prickly sida (Sida spinosa) Viola:

field pansy (Viola arvensis), wild pansy (Viola tricolor) Rubiaceae:

catchweed bedstraw (cleavers) (Galium aparine) Convolvulaceae:

ivyleaf morningglory (Ipomoea hederacea), tall morningglory (Ipomoea purpurea), entireleaf morningglory (Ipomoea hederacea var. integriuscula), pitted morningglory (Ipomoea lacunosa), field bindweed (Convolvulus arvensis) Labiatae:

red deadnettle (Lamium purpureum), henbit (Lamium amplexicaule) Solanaceae:

jimsonweed (Datura stramonium), black nightshade (Solanum nigrum) Scrophulariaceae:

birdseye speedwell (Veronica persica), ivyleaf speedwell (Veronica hederaefolia) Compositae:

common cocklebur (Xanthium pensylvanicum), common sunflower (Helianthus annuus), scentless chamomile (Matricaria inodora), corn marigold (Chrysanthemum segetum), pineappleweed (Matricaria matricarioides), common ragweed (Ambrosia artemisiifolia), giant ragweed (Ambrosia trifida), horseweed (Erigeron canadensis), Japanese mugwort (Artemisia princeps), tall goldenrod (Solidago altissima) Boraginaceae:

field forget-me-not (Myosotis arvensis) Asclepiadaceae:

common milkweed (Asclepias syriaca) Euphorbiaceae:

sun spurge (Euphorbia helioscopia), spotted spurge (Euphorbia maculata) Gramineae:

barnyardgrass (Echinochloa crus-galli), green foxtail (Setaria viridis), giant foxtail (Setaria faberi), large crabgrass (Digitaria sanguinalis), goosegrass (Eleusine indica), annual bluegrass (Poa annua), blackgrass (Alopecurus myosuroides), wild oat (Avena fatua), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*) Commelinaceae:

common dayflower (*Commelina communis*) Equisetaceae:

field horsetail (*Equisetum arvense*) Cyperaceae:

rice flatsedge (*Cyperus iria*), purple nutsedge (*Cyperus rotundus*), yellow nutsedge (*Cyperus esculentus*)

Further, some of the present compounds have no problematic phytotoxicity on main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (*Gossypium spp.*), sugar beet (*Beta vulgaris*), peanut (*Arachis hypogaea*), sunflower (*Helianthus annuus*) and canola (*Brassica napus*); garden crops such as flowers and ornamental plants; and vegetable crops.

The present compounds can attain effective control of unfavorable weeds in the no-tillage cultivation. Further, some of them exhibit no problematic phytotoxicity on crop plants such as soybean, corn and wheat.

The present compounds have herbicidal activity against various unfavorable weeds as recited below under the flooding treatment on paddy fields. Gramineae:

barnyardgrass (*Echinochloa oryzicola, Echinochloa crus-galli*) Scrophulariaceae:

common falsepimpernel (*Lindernia procumbens*) Lythraceae:

Rotala indica, *Ammannia multiflora* Elatinaceae:

*Elatine triandra* Cyperaceae:

smallflower umbrellaplant (*Cyperus difformis*), hardstem bulrush (*Scirpus juncoides*), needle spikerush (*Eleocharis acicularis*), *Cyperus serotinus, Eleocharis kuroguwai* Pontederiaceae:

*Monochoria vaginalis* Alismataceae:

*Sagittaria pygmaea, Sagittaria trifolia, Alisma canaliculatum* Potamogetonaceae:

roundleaf pondweed (*Potamogeton distinctus*) Umbelliferae:

*Oenanthe javanica*

Further, some of the present compounds have no problematic phytotoxicity on transplanted paddy rice or directly-sowed paddy rice.

The present compounds can attain effective control of various unfavorable weeds in orchards, grasslands, lawns, forests, waterways, canals or other non-cultivated lands.

The present compounds also have herbicidal activity against various aquatic plants such as water hyacinth (*Eichhornia crassipes*), which will grow in waterways, canals or the like.

When the present compound is used as an active ingredient of herbicides, it is usually mixed with solid or liquid carriers or diluents, surfactants and other auxiliary agents, and formulated into emulsifiable concentrates, wettable powders, flowables, granules, concentrated emulsions, water-dispersible granules, solutions or other formulations.

Each of these formulations may contain the present compound as an active ingredient at an amount of 0.001% to 90% by weight, preferably 0.003% to 80% by weight, based on the total weight of the formulation.

Examples of the solid carrier or diluent include fine powders or granules of the following materials: mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrated silicon oxide. Examples of the liquid carrier or diluent include aromatic hydrocarbons such as methylnaphthalene, phenylxylylethane and alkylbenzenes (e.g., xylene); alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, water, and the like.

Examples of the surfactant used for emulsification, dispersing or spreading include surfactants of the anionic type, such as alkylsulfates, alkylsulfonates, alkylarylsulfonates, dialkylsulfosuccinates and phosphates of polyoxyethylene alkylaryl ether; and surfactants of the nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent used for formulation include ligninsulfonates, alginates, polyvinyl alcohol, gum arabic, carboxymethyl cellulose (CMC) and isopropyl acid phosphate (PAP).

The present compound is usually formulated and used for pre-emergence or post-emergence control of unfavorable weeds by soil treatment, foliar treatment or flooding treatment on upland fields or paddy fields. The soil treatment includes soil surface treatment and soil incorporation. The foliar treatment includes application over the plants and directed application to the weeds to keep any chemical off the crop foliage.

In some cases, the present compound can be used in combination with other herbicides to enhance its herbicidal activity. Further, the present compound can also be used in combination with insecticides, acaricides, nematocides, fungicides, plant growth regulators, fertilizers, soil improver, and the like.

When the present compound is used as an active ingredient of herbicides, the application amount is usually in the range of 0.5 to 10,000 g, preferably 1 to 5000 g, per hectare, although it may vary depending upon the prevailing weather conditions; formulation type used, application timing, application method, soil involved, crop and weed species, and the like. In the case of emulsifiable concentrates, wettable powders, flowables, concentrated emulsions, water-dispersible granules or solutions, the formulation is usually applied at a prescribed amount after diluted with water having a volume of about 10 to 5000 liters per hectare, if necessary, with the addition of an adjuvant such as a spreading agent. In the case of granules, some types of flowables or solutions, the formulation is usually applied as such without any dilution.

Examples of the adjuvant include, in addition to the above-recited surfactants, polyoxyethylene resin acids (esters), ligninsulfonates, abietates, dinaphthylmethanedisulfonates, crop oil concentrates and vegetable oils such as soybean oil, corn oil, cotton seed oil and sunflower oil.

The present compound can be used as an active ingredient of harvesting aids such as defoliants and desiccating agents for cotton (*Gossypium spp.*) and desiccating agents for potato (*Solanum tuberosum*). In that case, the present compound is usually formulated in the same manner as the case where it is used as an active ingredient of herbicides, and used alone or in combination with other harvesting aids for foliar treatment before the harvesting of crops.

The present invention will be further illustrated by the following Production Examples, Formulation Examples and Test examples, which are not to be construed to limit the scope thereof.

The following will describe Production Examples of the present compounds. In these Production Examples, the present compounds are designated by the respective compound numbers shown in Tables 1 to 13.

PRODUCTION EXAMPLE 1

To 0.58 g of 1-(4-chloro-6-fluoro-3-hydroxy-2-(2,3-epoxy-2-methylpropyl) phenyl)-3-methyl-4-trifluoromethyl-1,2,3,6-tetrahydropyrimidine-2,6-dione were added 5 ml of pyridine and 5 ml of acetic anhydride, and the mixture was stirred at room temperature for 2 hours. After completion of the reaction, the reaction mixture was concentrated, and the residue was subjected to preparative thin layer silica gel chromatography, which afforded 0.5 g of the present compound 8-71.

$^1$H-NMR δ(ppm) [250 MHz, CDCl$_3$/TMS]: 1.13 (3×1/2 H, s), 1.16 (3×1/2 H, s), 2.39 (3 H, s), 2.47 (2H, m), 2.30–2.60 (1H, m), 2.97 (1/2 H, d, J=1.52 Hz), 3.08 (1/2 H, d, J=15 Hz), 3.54 (3H, s), 6.30 (1/2 H, s), 6.36 (1/2 H, s), 7.30 (1/2 H, d, J=8.7 Hz), 7.31 (1/2 H, d, J=8.6 Hz)

PRODUCTION EXAMPLE 2

First, 0.75 g of N-(3-acetyloxy-2-allyl-4-chloro-6-fluorophenyl)-3,4,5,6-tetrahydrophthalimide was dissolved in 10 ml of chloroform, to which 1.0 g of m-chloroperbenzoic acid was added at 0° C., and the mixture was stirred for 19 hours, while slowly warming to room temperature. After completion of the reaction, the reaction mixture was subjected to phase separation with ethyl acetate and aqueous sodium sulfite solution, and the organic layer was successively washed with saturated aqueous sodium bicarbonate solution and water, dried and concentrated. The residue was preparative thin layer silica gel chromatography, which afforded 0.50 g of the present compound 1-21.

$^1$H-NMR δ(ppm) [60 MHz, CDCl$_3$/TMS]: 1.60–1.90 (4H, m), 2.30 (3H, s), 2.30–2.50 (4H, m), 2.55–3.00 (3H, m), 7.60 (1H, d, J=9 Hz)

PRODUCTION EXAMPLE 3

In this example, 0.7 g of the present compound 1-71 was obtained in the same manner as described in Production Example 2, except that 0.7 g of N-(3-acetyloxy-4-chloro-6-fluoro-2-(2-methyl-2-propenyl)phenyl)-3,4,5,6-tetrahydrophthalimide and 0.7 g of m-chloroperbenzoic acid were used as the starting materials.

$^1$H-NMR δ(ppm) [250 MHz, CDCl$_3$/TMS]: 1.50 (3H, s), 1.80–1.90 (4H, m), 2.39 (3H, s), 2.40–2.50 (4H, m), 2.48 (2H, s), 2.70 (2H, d, J=14.9 Hz), 2.92 (2H, d, J=14.9 Hz), 7.26 (1H, d, J=8.6 Hz)

PRODUCTION EXAMPLE 4

In this example, 0.36 g of the present compound 1-76 was obtained in the same manner as described in Production Example 2, except that 0.5 g of N-(4-chloro-6-fluoro-3-(4-methoxyphenylcarbonyloxy)-2-(2-methyl-2-propenyl) phenyl)-3,4,5,6-tetrahydrophthalimide and 0.6 g of m-chloroperbenzoic acid were used as the starting materials.

$^1$H-NMR δ(ppm) [250 MHz, CDCl$_3$/TMS]: 1.41 (3H, s), 1.65–1.90 (4H, m), 2.35–2.50 (6H, m), 2.78 (1H, d, J=14 Hz), 2.90 (1H, d, J=14 Hz), 3.91 (3H, s), 7.02 (2H, d, J=7.0 Hz), 7.30 (1H, d, J=8.6 Hz), 8.18 (2H, d, J=7.0 Hz)

PRODUCTION EXAMPLE 5

In this example, 0.6 g of the present compound 1-79 was obtained in the same manner as described in Production Example 2, except that 0.6 g of N-(4-chloro-6-fluoro-3-(methylaminocarbonyloxy)-2-(2-methyl-2-propenyl) phenyl)-3,4,5,6-tetrahydrophthalimide and 0.5 g of m-chloroperbenzoic acid were used as the starting materials.

$^1$H-NMR δ(ppm) [250 MHz, CDCl$_3$/TMS]: 1.59 (3H, s), 1.75–1.90 (4H, m), 2.35–2.55 (6H, m), 2.77 (1H, d, J=14.9 Hz), 2.85–3.00 (3H, m), 5.22 (1H, br), 7.24 (1H, d, J=8.7 Hz)

PRODUCTION EXAMPLE 6

In this example, 0.46 g of the present compound 1-80 was obtained in the same manner as described in Production Example 2, except that 0.6 g of N-(4-chloro-3-(dimethylaminocarbonyloxy)-6-fluoro-2-(2-methyl-2-propenyl)phenyl)-3,4,5,6-tetra-hydrophthalimide and 0.5 g of m-chloroperbenzoic acid were used as the starting materials.

$^1$H-NMR δ(ppm) [250 MHz, CDCl$_3$/TMS]: 1.68 (3H, s), 1.75–1.90 (4H, m), 2.35–2.45 (4H, m), 2.49 (2H, s), 2.78 (1H, d, J=14.8 Hz), 2.89 (1H, d, J=1.48 Hz), 3.05 (3H, s), 3.18 (3H, s), 7.22 (1H, d, J=8.6 Hz)

PRODUCTION EXAMPLE 7

In this example, 0.84 g of the present compound 1-95 was obtained in the same manner as described in Production Example 2, except that 0.9 g of N-(4-chloro-6-fluoro-3-methanesulfonyloxy-2-(2-methyl-2-propenyl)phenyl)-3,4,5,6-tetrahydrophthalimide and 0.8 g of m-chloroperbenzoic acid were used as the starting materials.

1H-NMR δ(ppm) [300 MHz, CDCl$_3$/TMS]: 1.22 (3H, s), 1.75–1.90 (4H, m), 2.35–2.50 (6H, m), 2.96 (1H, d, J=15.3 Hz), 3.33 (1H, d, J=15.3 Hz), 3.47 (3H, s), 7.28 (1H, d, J=8.4 Hz)

PRODUCTION EXAMPLE 8

In this example, 0.52 g of the present compound 8-21 was obtained in the same manner as described in Production Example 2, except that 0.7 g of 1-(3-acetyloxy-2-allyl-4-chloro-6-fluorophenyl)-3-methyl-4-trifluoromethyl-1,2,3,6-tetrahydropyrimidine-2,6-dione and 0.43 g of m-chloroperbenzoic acid were used as the starting materials.

$^1$H-NMR δ(ppm) [300 MHz, CDCl$_3$/TMS]: 2.40 (3H, s), 2.60–2.95 (5H, m), 3.55 (3H, s), 6.33 (1/2H, s), 6.36 (1/2H, s), 7.30 (1H, d, J=8.6 Hz)

PRODUCTION EXAMPLE 9

In this example, 0.69 g of the present compound 8-22 was obtained in the same manner as described in Production Example 2, except that 0.9 g of 1-(2-allyl-4-chloro-6-fluoro-3-propionyloxyphenyl)-3-methyl-4-trifluoromethyl-1,2,3,6-tetrahydropyrimidine- 2,6-dione and 0.95 g of m-chloroperbenzoic acid were used as the starting materials.

$^1$H-NMR δ(ppm) [250 MHz, CDCl$_3$/TMS]: 1.32 (3H, t, J=7.6 Hz), 2.38 (2H, m), 2.60–3.00 (5H, m), 3.55 (3H, s), 6.33 (1/2H, s), 6.36 (1/2H, s), 7.31 (1H, d, J=8.6 Hz)

PRODUCTION EXAMPLE 10

In this example, 0.8 g of the present compound 8-24 was obtained in the same manner as described in Production Example 2, except that 0.8 g of 1-(2-allyl-4-chloro-6-fluoro- 3-pivaloyloxyphenyl)-3-methyl-4-trifluoromethyl-1,2,3,6-tretrahydropyrimidine-2,6-dione and 1.0 g of m-chloroperbenzoic acid were used as the starting materials.

$^1$H-NMR δ(ppm) [300 MHz, CDCl$_3$/TMS]: 1.42 (9H, s), 2.35–3.00 (5H, m), 6.33 (1/2H, s), 6.36 (1/2H, s), 7.30 (1H, d, J=8.6 Hz)

PRODUCTION EXAMPLE 11

In this example, 0.54 g of the present compound 8-25 was obtained in the same manner as described in Production Example 2, except that 0.8 g of 1-(2-allyl-3-benzoyloxy-4-chloro-6-fluorophenyl)-3-methyl -4-trifluoromethyl-1,2,3,6-tetrahydropyrimidine-2,6-dione and 1.0 g of m-chloroperbenzoic acid were used as the starting materials.

$^1$H-NMR δ(ppm) [300 MHz, CDCl$_3$/TMS]: 2.30–3.00 (5H, m), 3.56 (3H, s), 6.34 (1/2H, s), 6.38 (1/2H, s), 7.35 (1H, d, J=8.7 Hz), 7.48–7.72 (3, m), 8.10–8.24 (2H, m)

PRODUCTION EXAMPLE 12

In this example, 2.26 g of the present compound 8-32 was obtained in the same manner as described in Production Example 2, except that 2.5 g of 1-(2-allyl-3-benzyloxy-4-chloro-6-fluorophenyl)-3-methyl-4-trifluoromethyl-1,2,3,6-tetrahydropyrimidine-2,6-dione and 2.0 g of m-chloroperbenzoic acid were used as the starting materials.

$^1$H-NMR δ(ppm) [250 MHz, CDCl$_3$/TMS]: 2.35 (m), 2.59 (m), 2.80–3.06 (m), (these correspond to 5H in total), 3.55 (3H, s), 4.98 (1H, d, J=10.8 Hz), 5.05 (1H, d, J=10.8 Hz), 6.33 (1/2H, s), 6.36 (1/2H, s), 7.29 (1H, d, J=8.9 Hz), 7.36–7.50 (5H, m)

PRODUCTION EXAMPLE 13

In this example, 0.6 g of the present compound 8-51 was obtained in the same manner as described in Production Example 2, except that 0.63 g of 1-(4-chloro-6-fluoro-3-methoxy-2-(2-methyl-2-propenyl)phenyl)-3-methyl-4-trifluoromethyl-1,2,3,6-tetrahydropyrimidine-2,6-dione and 0.7 g of m-chloroperbenzoic acid were used as the starting materials.

$^1$H-NMR δ(ppm) [250 MHz, CDCl$_3$/TMS]: 1.14 (3×1/2H, s), 1.18 (3×1/2H, s), 2.34 (1/2H, d, J=14.7 Hz), 2.50 (2H, m), 2.62 (1/2H, d, J=14.8 Hz), 3.15 (1/2H, d, J=14.8 Hz), 3.30 (1/2H, d, J=14.7 Hz), 3.54 (3H, s), 3.87 (3H, s), 6.29 (1/2H, s), 6.37 (1/2H, s), 7.23 (1/2H, d, J=8.8 Hz), 7.24 (1/2H, d, J=8.8 Hz)

PRODUCTION EXAMPLE 14

In this example, 0.25 g of the present compound 8-53 was obtained in the same manner as described in Production Example 2, except that 0.25 g of 1-(4-chloro-6-fluoro-3-isopropoxy-2-(2-methyl-2-propenyl)phenyl)-3-methyl-4-trifluoromethyl-1,2,3,6-tetrahydropyrimidine-2,6-dione and 0.2 g of m-chloroperbenzoic acid were used as the starting materials.

$^1$H-NMR δ(ppm) [250 MHz, CDCl$_3$/TMS]: 1.09 (3×1/2H, s), 1.13 (3×1/2H, s), 1.23–1.43 (6H, m), 2.34 (1/2H, d, J=14.6 Hz), 2.48 (2H, m), 2.63 (1/2H, d, J=14.8 Hz), 3.22 (1/2H, 14.8 Hz), 3.39 (1/2H, d, J=14.6 Hz), 3.53 (3H, s), 4.52 (1H, m), 6.27 (1/2H, s), 6.37 (1/2H, s), 7.23 (1/2H, d, J=8.8 Hz), 7.24 (1/2H, d, J=8.8 Hz)

PRODUCTION EXAMPLE 15

In this example, 0.46 g of the present compound 8-56 was obtained in the same manner as described in Production Example 2, except that 0.5 g of 1-(4-chloro-6-fluoro-3-methoxymethyloxy-2(2-methyl-2-propenyl)phenyl)-3-methyl -4-trifluoromethyl-1,2,3,6-tetrahydropyrimidine-2,6-dione and 0.5 g of m-chloroperbenzoic acid were used as the starting materials.

$^1$H-NMR δ(ppm) [300 MHz, CDCl$_3$/TMS]: 1.16 (3×1/2H, s), 1.19 (3×1/2H, s), 2.37 (1/2H, d, J=14.8 Hz), 2.48 (2H, m), 2.49 (1/2H, d, J=15.0 Hz), 3.28 (1/2H, d, J=15.0 Hz), 3.47 (1/2H, d, J=14.8 Hz), 3.54 (3H, s), 3.60 (3H, s), 5.06–5.16 (2H, m), 6.29 (1/2H, s), 6.36 (1/2H, s), 7.24 (1H, d, J=8.8 Hz)

PRODUCTION EXAMPLE 16

First, 1.0 g of 1-(4-chloro-6-fluoro-3-hydroxy-2-(2,3-epoxy-2-methyl-propyl)phenyl)-3-methyl-4-trifluoromethyl-1,2,3,6-tetrahydropyrimidine-2,6-dione was dissolved in 10 ml of dimethylsulfoxide and 5 ml of acetic anhydride, and the mixture was stirred at room temperature for 24 hours. After completion of the reaction, the reaction mixture was subjected to phase separation with ethyl acetate and saturated aqueous sodium bicarbonate solution, and the organic layer was washed with water, dried and concentrated. The residue was preparative thin layer silica gel chromatography, which afforded 0.9 g of the present compound 8-60.

$^1$H-NMR δ(ppm) [60 MHz, CDCl$_3$/TMS]: 1.15 (3H, s), 2.0–3.0 (7H, m), 3.55 (3H, s), 5.12 (2H, s), 6.30 (1/2H, s), 6.33 (1/2H, s), 7.30 (1H, d, J=8 Hz).

PRODUCTION EXAMPLE 17

In this example, 0.5 g of the present compound 8-66 was obtained in the same manner as described in Production Example 2, except that 0.5 g of 1-(4-chloro-6-fluoro-2-(2-methyl-2-propenyl)-3-propargyloxyphenyl)-3-methyl-4-trifluoromethyl-1,2,3,6-tetrahydropyrimidine-2,6-dione and 0.32 g of m-chloroperbenzoic acid were used as the starting materials.

$^1$H-NMR δ(ppm) [250 MHz, CDCl$_3$/TMS]: 1.14 (3×1/2H, s), 1.19 (3×1/2H, s), 2.37 (1/2H, d, J=14.8 Hz), 2.50 (2H, m), 2.58 (1H, t, J=2.1 Hz), 2.70 (1/2H, d, J=14.9 Hz), 3.28 (1/2H, d, J=14.9 Hz), 3.50 (1/2H, d, J=14.8 Hz), 3.54 (3H, s), 4.72–4.76 (2H, m), 6.29 (1/2H, s), 6.37 (1/2H, s), 7.24 (1/2H, d, J=8.9 Hz), 7.25 (1/2H, d, J=8.5 Hz)

PRODUCTION EXAMPLE 18

In this example, 0.8 g of the present compound 8-74 was obtained in the same manner as described in Production Example 2, except that 0.8 g of 1-(4-chloro-6-fluoro-2-(2-methyl-2-propenyl)-3-trimethylacetyloxyphenyl)-3-methyl-4-trifluoromethyl-1,2,3,6-tetrahydropyrimidine-2,6-dione and 1.0 g of m-chloroperbenzoic acid were used as the starting materials.

$^1$H-NMR δ(ppm) [250 MHz, CDCl$_3$/TMS]: 1.18 (3H, s), 1.42 (9H, s), 2.30–3.00 (4H, m), 3.54 (3H, s), 6.29 (1/2H, s), 6.35 (1/2H,s), 7.28 (1/2H, s), 8.8 Hz), 7.29 (1/2H, d, J=8.6 Hz)

PRODUCTION EXAMPLE 19

In this example, 0.8 g of the present compound 8-75 was obtained in the same manner as described in Production Example 2, except that 0.8 g of 1-(3-benzoyloxy-4-chloro-6-fluoro-2-(2-methyl-2-propenyl)phenyl)-3-methyl-4-trifluoromethyl-1,2,3,6-tetrahydropyrimidine-2,6-dione and 1.0 g of m-chloroperbenzoic acid were used as the starting materials.

¹H-NMR δ(ppm) [300 MHz, CDCl₃/TMS]: 1.14 (3H, s), 2.43 (2H, m), 2.65 (1H, br), 3.01 (1H, br), 3.55 (3H, s), 6.31 (1/2H,s), 6.38 (1/2H, s), 7.35 (1/2H, d, J=8.6 Hz), 7.36 (1/2H, d, J=8.6 Hz), 7.45–7.72 (3H, m), 8.09–8.25 (2H, m)

PRODUCTION EXAMPLE 20

In this example, 0.33 g of the present compound 8-76 was obtained in the same manner as described in Production Example 2, except that 0.5 g of 1-(4-chloro-6-fluoro-3-(4-methoxybenzoyloxy)-2-(2-methyl-2-propenyl)phenyl)-3-methyl-4-trifluoromethyl-1,2,3,6-tetrahydropyrimidine-2,6-dione and 0.6 g of m-chloroperbenzoic acid were used as the starting materials.

¹H-NMR δ(ppm) [300 MHz, CDCl₃/TMS]: 1.15 (3H, s), 2.44 (2H, m), 2.65 (1H, br), 3.03 (1H, br), 3.56 (3H, s), 3.92 (3H,s), 6.32 (1/2H, s), 6.38 (1/2H, s), 7.03 (2H, d, J=8.9 Hz), 7.34 (1/2H, d, J=8.6 Hz), 7.35 (1/2H, d, J=8.6 Hz), 8.19 (2H, d, J=8.9 Hz)

PRODUCTION EXAMPLE 21

In this example, 0.6 g of the present compound 8-79 was obtained in the same manner as described in Production Example 2, except that 0.6 g of 1-(4-chloro-6-fluoro-3-methylaminocarbonyloxy-2-(2-methyl-2-propenyl)phenyl)-3-methyl-4-trifluoromethyl-1,2,3,6-tetrahydropyrimidine-2,6-dione and 0.5 g of m-chloroperbenzoic acid were used as the starting materials.

¹H-NMR δ(ppm) [300 MHz, CDCl₃/TMS]: 1.14 (3×1/2H, s), 1.17 (3×1/2H, s), 2.39 (1/2H, d, J=15.1 Hz), 2.49 (2H, m), 2.62 (1/2H, d, J=15.1 Hz), 2.92 (3×1/2H, s), 2.94 (3×1/2H, s), 2.99 (1/2H, d, J=15.1 Hz), 3.11 (1/2H, d, J=15.1 Hz), 3.54 (3H, s), 5.23 (1H, br), 6.30 (1/2H, s), 6.36 (1/2H, s), 7.27 (1H, d, J=8.6 Hz)

PRODUCTION EXAMPLE 22

In this example, 0.6 g of the present compound 8-80 was obtained in the same manner as described in Production Example 2, except that 0.6 g of 1-(4-chloro-3-dimethylaminocarbonyloxy-6-fluoro-2-(2-methyl-2-propenyl)phenyl)-3-methyl-4-trifluoromethyl-1,2,3,6-tetrahydropyrimidine-2,6-dione and 0.5 g of m-chloroperbenzoic acid were used as the starting materials.

¹H-NMR δ(ppm) [300 MHz, CDCl₃/TMS]: 1.15 (3×1/2H, s), 1.18 (3×1/2H, s), 2.40 (1/2H, d, J=15.4 Hz), 2.49 (2H, s), 2.62 (1/2H, d, J=15.2 Hz), 2.97 (1/2H, d, J=15.2 Hz), 3.04 (3H, s), 3.09 (1/2H, d, J=15.4 Hz), 3.17 (3H, s), 3.54 (3H, s), 6.29 (1/2H, s), 6.36 (1/2H, s), 7.28 (1H, d, J=7.8 Hz)

PRODUCTION EXAMPLE 23

In this example, 0.6 g of the present compound 8-86 was obtained in the same manner as described in Production Example 2, except that 0.6 g of 1-(4-chloro-6-fluoro-3-methoxycarbonylmethyloxy-2-(2-methyl-2-propenyl) phenyl)-3-methyl-4-trifluoromethyl-1,2,3,6-tetrahydropyrimidine-2,6-dione and 0.34 g of m-chloroperbenzoic acid were used as the starting materials.

¹H-NMR δ(ppm) [60 MHz, CDCl₃/TMS]: 1.20 (3H, s), 2.40–2.80 (1H, m), 2.45 (2H, s), 3.23–3.50 (1H, m), 3.50 (3H, s), 3.78 (3H, s), 4.60 (2H, s), 6.21 (1/2H, s), 6.30 (1/2H, s), 7.15 (1H, d, J=8 Hz)

PRODUCTION EXAMPLE 24

In this example, 0.8 g of the present compound 8-87 was obtained in the same manner as described in Production Example 2, except that 1.0 g of 1-(4-chloro-3-ethoxycarbonylmethyloxy-6-fluoro-2-(2-methyl-2-propenyl)phenyl)-3-methyl-4-trifluoromethyl-1,2,3,6-tetrahydropyrimidine-2,6-dione and 0.8 g of m-chloroperbenzoic acid were used as the starting materials.

1H-NMR δ(ppm) [250 MHz, CDCl₃/TMS]: 1.17 (3×1/2H, s), 1.21 (3×1/2H, s), 1.32 (3H, t, J=7.1 Hz), 2.33 (1/2H, d, J=14.7 Hz), 2.48 (2×1/2H, s), 2.50 (2×1/2H, s), 2.67 (1/2H, d, J=14.8 Hz), 3.41 (1/2H, d, J=14.8 Hz), 3.53 (3H, s), 3.61 (1/2H, d, J=14.7 Hz), 3.29 (2H, q, J=7.1 Hz), 4.51–4.79 (2H, m), 6.29 (1/2H, s), 6.37 (1/2H, s), 7.23 (1/2H, d, J=8.7 Hz), 7.24 (1/2H, d, J=8.6 Hz)

PRODUCTION EXAMPLE 25

In this example, 0.4 g of the present compound 8-92 was obtained in the same manner as described in Production Example 2, except that 1.0 g of 1-(4-chloro-3-(1-ethoxycarbonylethyloxy)-6-fluoro-2-(2-methyl-2-propenyl) phenyl)-3-methyl-4-trifluoromethyl-1,2,3,6-tetrahydropyrimidine-2,6-dione and 0.6 g of m-chloroperbenzoic acid were used as the starting materials.

¹H-NMR δ(ppm) [300 MHz, CDCl₃/TMS]: 1.10–1.32 (6H, m), 1.47–1.68 (3H, m), 2.42–2.53 (4H, m), 3.53 (3H, s), 4.11–84.29 (2H, m), 4.91–4.99 (1m), 6.27 (1/2H, s), 6.35 (1/2H, s), 7.22 (1/2H, d, J=8.7 Hz), 7.23 (1/2H, d, J=8.6 Hz)

PRODUCTION EXAMPLE 26

In this example, 0.43 g of the present compound 8-95 was obtained in the same manner as described in Production Example 2, except that 0.5 g of 1-(4-chloro-6-fluoro-3-methanesulfonyloxy-2-(2-methyl-2-propenyl)phenyl)-3-methyl-4-trifluoromethyl-1,2,3,6-tetrahydropyrimidine-2,6-dione and 0.5 g of m-chloroperbenzoic acid were used as the starting materials.

¹H-NMR δ(ppm) [250 MHz, CDCl₃/TMS]: 1.20 (3×1/2H, s), 1.24 (3×1/2H, s), 2.47 (2×1/2H, s), 2.48 (2×1/2H, s), 2.53 (1/2H, d, J=15.6 Hz), 2.83 (1/2H, d, J=15.7 Hz), 3.38 (1/2H, d, J=15.7 Hz), 3.48 (3H, s), 3.53 (3H, s), 3.57 (1/2H, d, J=15.6 Hz), 6.30 (1/2H, s), 6.35 (1/2H, s), 7.32 (1/2H, d, J=8.4 Hz), 7.33 (1/2H, d, J=8.4 Hz)

PRODUCTION EXAMPLE 27

In this example, 0.4 g of the present compound 8-121 was obtained in the same manner as described in Production Example 2, except that 0.5 g of 1-(3-acetyloxy-2-allyl-4-chlorophenyl)-3-methyl-4-fluoromethyl-1,2,3,6-tetrahydropyrimidine-2,6-dione and 0.5 g of m-chloroperbenzoic acid were used as the starting materials.

¹H-NMR δ(ppm) [250 MHz, CDCl₃/TMS]: 2.40 (3H, s), 2.04–3.00 (5H, m), 3.54 (3H, s), 6.33 (1/2H, s), 6.37 (1/2H, s), 7.02 (1/2H, d, J=8.5 Hz), 7.04 (1/2H, d, J=8.5 Hz), 7.49 (1H, d, J=8.5 Hz)

PRODUCTION EXAMPLE 28

In this example, 0.57 g of the present compound 1-59 was obtained in the same manner as described in Production Example 2, except that 0.58 g of N-(4-chloro-6-fluoro-3-methoxyethoxymethoxy-2-(2-methyl-2-propenyl)phenyl)-3,4,5,6-tetrahydrophthalimide and 0.34 g of m-chloroperbenzoic acid were used as the starting materials.

¹H-NMR δ(ppm) [250 MHz, CDCl₃/TMS]: 1.17 (3H, s), 1.78–1.90 (4H, m), 2.35–2.50 (4H, m), 2.47 (2H, s), 2.87 (1H, d, J=15 Hz), 3.16 (1H, d, J=15 Hz), 3.40 (3H, s), 3.60 (2H, m), 3.95 (2H, m), 5.20 (2H, q, J=4 Hz), 7.19 (1H, d, J=8 Hz)

The following will describe Reference Production Example of the compound [3] which is a starting compound used in the production of the present compounds.

REFERENCE PRODUCTION EXAMPLE 1

First, 50 g of 1-[4-chloro-6-fluoro-3-hydroxy-2-(2-methyl-2-propenyl)phenyl]-3-methyl-4-trifluoromethyl-1,2,3,6-tetrahydropyrimidine-2,6-dione was dissolved in 500 ml of chloroform, to which 30.0 g of m-chloroperbenzoic acid was added, and the reaction was allowed to proceed at 60° C. for 4.5 hours. After completion of the reaction, the reaction mixture was cooled to room temperature and subjected to phase separation with chloroform and aqueous sodium sulfite solution. The organic layer was successively washed with saturated aqueous sodium bicarbonate solution and water, dried and concentrated. The residue was recrystallized to afford 46 g of 1-[4-chloro-6-fluoro-3-hydroxy-2-(2,3-epoxy-2-methylpropyl)phenyl]-3-methyl-4-trifluoromethyl-1,2,3,6-tetrahydropyrimidine-2,6-dione.

$^1$H-NMR δ(ppm) [60 MHz, CDCl$_3$/TMS]: 1.29 (1/2×3H, s), 1.31 (1/2×3H, s), 2.75 (3H, m), 3.10 (1H, m), 3.58 (3H, s), 6.31 (1H, s), 7.20 (1H, d, J=8 Hz), 7.45 (1H, s)

The following will describe Reference Production Example of the compound [2] which is a starting compound used in the production of the present compounds.

REFERENCE PRODUCTION EXAMPLE 2

First, 1.0 g of 1-[4-chloro-6-fluoro-3-hydroxy-2-(2-methyl-2-propenyl)phenyl]-3-methyl-4-trifluoromethyl-1,2,3,6-tetrahydropyrimidine-2,6-dione was dissolved in 15 ml of N,N-dimethylformamide, to which 0.43 g of potassium carbonate and 0.4 ml of methyl bromoacetate were added, and the mixture was stirred at room temperature for 30 minutes. After completion of the reaction, the reaction mixture was poured into water and extracted with diethyl ether. The organic layer was dried and concentrated. The residue was subjected to silica gel chromatography, which afforded 1.0 g of 1-[4-chloro-6-fluoro-3-methoxycarbonylmethyloxy-2-(2-methyl-2-propenyl)phenyl]-3-methyl-4-trifluoromethyl-1,2,3,6-tetrahydropyrimidine-2,6-dione.

$^1$H-NMR δ(ppm) [250 MHz, CDCl$_3$/TMS]: 1.60 (3H, s), 3.34 (1H, d, J=15.4 Hz), 3.49 (1H, d, J=15.4 Hz), 3.52 (3H, s), 3.81 (3H, s), 4.45 (1H, s), 4.60 (2H, s), 4.66 (1H, s), 6.32 (1H, s), 7.22 (1H, d, J=8.6 Hz)

The following will describe Reference Production Example of the compound [7] which is a starting compound used in the production of the present compounds.

REFERENCE PRODUCTION EXAMPLE 3

First, 21.6 g of 1-[4-chloro-2-fluoro-5-(2-methyl-2-propenyloxy)phenyl]-3-methyl-4-trifluoromethyl-1,2,3,6-tetrahydropyrimidine-2,6-dione was dissolved in 50 ml of N,N-diethylaniline, and the solution was heated under reflux for 4 hours. After completion of the reaction, the reaction mixture was cooled to room temperature and extracted with diethyl ether. The extract was washed with diluted hydrochloric acid, dried and concentrated. The residue was subjected to silica gel chromatography (eluent; hexane: ethyl acetate=2:1), which 19.5 g of 1-[4-chloro-6-fluoro-3-hydroxy-2-(2-methyl-2-propenyl)phenyl]-3-methyl-4-trifluoromethyl-1,2,3,6-tetrahydropyrimidine-2,6-dione.

$^1$H-NMR δ(ppm) [60 MHz, CDCl$_3$/TMS]: 1.60 (3H, s), 3.28 (2H, s), 3.48 (3H, s), 4.4–4.6 (1H, m), 4.6–4.8 (1H, m), 5.76 (1H, s), 6.36 (1H, s), 7.09 (1H, d, J=10 Hz)

The following will describe Reference Production Examples of the compound [9].

REFERENCE PRODUCTION EXAMPLE 4

To a suspension of 1.4 g of N-(4-chloro-2-fluoro-5-allyloxy)phenyl-N'-methylthiourea and 0.5 g of sodium acetate in 20 ml of toluene is added 1.0 g of 3-bromo-1,1,1-trifluoroacetone, and the mixture is stirred under reflux. After completion of the reaction, the reaction mixture is poured into water. The organic layer is separated, washed with water, dried with magnesium sulfate and concentrated. The residue is mixed with 10 ml of concentrated sulfuric acid, and the mixture is stirred. The reaction mixture is poured onto ice and extracted with ethyl acetate. The organic layer is washed, dried with magnesium sulfate and concentrated. The residue is subjected to silica gel chromatography to give a compound of the formula:

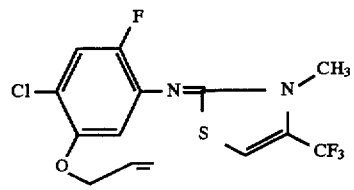

REFERENCE PRODUCTION EXAMPLE 5

To a suspension of 0.4 g of N-(4-chloro-2-fluoro-5-allyloxy)phenyl-N'-methylthiourea and 0.12 g of sodium acetate in 5 ml of ethanol is added 0.22 g of bromoacetic acid, and the mixture is stirred under reflux for 2 hours. After completion of the reaction, the reaction mixture is poured into water and extracted with ethyl acetate. The organic layer is washed with saturated sodium hydrogencarbonate solution, dried with magnesium sulfate and concentrated. The residue is subjected to silica gel chromatography to give a compound of the formula:

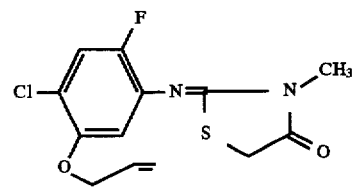

The following will describe Formulation Examples. In these Formulation Examples, the present compounds are designated by the respective compound numbers shown in Tables 1 to 13, and parts are by weight.

FORMULATION EXAMPLE 1

Fifty parts of each of the present compounds 1-21, 1-76, 1-79, 1-95, 8-22, 8-25, 8-51, 8-56, 8-75, 8-80, 8-92, 8-121 and 8-175, 3 parts of calcium ligninsulfonate, 2 parts of sodium laurylsulfate and 45 parts of synthetic hydrated silicon oxide are well pulverized and mixed to give a wettable powder for each compound.

FORMULATION EXAMPLE 2

Ten parts of each of the present compounds 1-32, 1-71, 1-80, 8-6, 8-21, 95 and 8-171, 14 parts of polyoxyethylene styryl phenyl ether, 6 parts of calcium dodecylbenzenesulfonate, 35 parts of xylene and 35 parts of cyclohexanone are well mixed to give an emulsifiable concentrate for each compound.

FORMULATION EXAMPLE 3

Two parts of each of the present compounds 1-21, 1-32, 1-71, 1-76, 1-79, 1-95, 8-6, 8-22, 8-25, 8-32, 8-53, 8-56, 8-60, 8-66, 8-75, 8-76, 8-79, 8-121, 8-171 and 8-175, 2 parts of synthetic hydrated silicon oxide, 2 parts of calcium ligninsulfonate, 30 parts of bentonite and 64 parts of kaoline clay are well pulverized and mixed, to which water is added, and the mixture is well kneaded, granulated and dried to give a granule for each compound.

The following Test Examples will demonstrate that the present compounds are useful as active ingredients of herbicides. The present compounds are designated by the respective compound numbers shown in Tables 1 to 13.

The herbicidal activity was evaluated at 6 levels with indices of 0 to 5, i.e., designated by the numeral "0", "1", "2", "3", "4" or "5", wherein "0" means that there was no or little difference in the degree of germination or growth between the treated and the untreated test plants at the time of examination, and "5" means that the test plants died complete or their germination or growth was completely inhibited. The herbicidal activity is excellent when rated at "5" or "4" but insufficient when rated at "3" or lower.

TEST EXAMPLE 1

Soil surface treatment

Cylindrical plastic pots of 10 cm in diameter and 10 cm in depth were filled with soil, and the seeds of ivyleaf morningglory (*Ipomoea hederacea*) and velvetleaf (*Abutilon theophrasti*) were sowed therein. Each of the test compounds 1-21, 1-79, 8-6, 8-21, 8-22, 8-25, 8-51, 8-56, 8-60, 8-71, 8-75, 8-79 and 8-80 was formulated into an emulsifiable concentrate according to Formulation Example 2, which was diluted with water to a prescribed concentration. The dilution was uniformly sprayed over the soil surface in the pots with a sprayer at a volume of 1000 liters per hectare. In this treatment, each of the test compounds was applied at an amount of 500 grams per hectare. After the spraying, the test plants were grown in a greenhouse for 19 days, and the herbicidal activity was examined.

As a result, it was found that all the test compounds exhibited the highest herbicidal activity "5" to both ivyleaf morningglory and velvetleaf.

TEST EXAMPLE 2

Foliar treatment

Cylindrical plastic pots of 10 cm in diameter and 10 cm in depth were filled with soil, and the seeds of velvetleaf (*Abutilon theophrasti*) were sowed therein and grown in a greenhouse for 12 days. Each of the test compounds 1-79, 1-80, 8-6, 8-21, 8-56, 8-60, 8-71 8-79, 8-80 and 8-92 was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. In this treatment, each of the test compounds was applied at an amount of 500 grams per hectare. After the spraying, the test plants were grown in the greenhouse for 19 days, and the herbicidal activity was examined.

As a result, it was found that all the test compounds exhibited the highest herbicidal activity "5" to velvetleaf.

TEST EXAMPLE 3

Flooding treatment

Cylindrical plastic pots of 9 cm in diameter and 11 cm in depth were filled with soil, and the seeds of barnyardgrass (*Echinochloa oryzicola*) were sowed therein. These pots were flooded to form a paddy field, and the test plants were grown in a greenhouse for 7 days. Each of the test compounds 1-32, 1-71, 1-76, 1-79, 1-95, 8-6, 8-21, 8-22, 8-25, 8-32, 8-53, 8-56, 8-60, 8-66, 8-71, 8-75, 8-76, 8-79, 8-121, 8-171 and 8-175 was formulated into an emulsifiable concentrate according to Formulation Example 2, which was diluted with water to a prescribed concentration. The dilution was applied to the water surface in the pots with a syringe at a volume of 5000 liters per hectare. In this treatment, each of the test compounds was applied at an amount of 250 grams per hectare. After the application, the test plants were grown in the greenhouse for 19 days, and the herbicidal activity was examined.

As a result, it was found that all the test compounds exhibited the highest herbicidal activity "5" to barnyardgrass.

What is claimed is:

1. A compound of the formula:

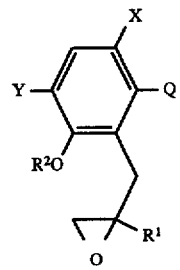

[1]

wherein X is hydrogen, fluorine or chlorine;

Y is fluorine, chlorine or bromine;

$R^1$ is hydrogen or $C_1$–$C_3$ alkyl;

$R^2$ is $C_1$–$C_6$ alkyl, $C_1$–$C_6$ haloalkyl, $C_1$–$C_6$ alkoxy ($C_1$–$C_6$) alkyl, $C_1$–$C_6$ alkoxy ($C_1$–$C_6$) alkoxy ($C_1$–$C_6$) alkyl, $C_1$–$C_6$ alkylthio ($C_1$–$C_6$) alkyl, $C_3$–$C_6$ alkenyl, $C_3$–$C_6$ haloalkenyl, $C_3$–$C_6$ alkynyl, $C_3$–$C_6$ haloalkynyl or $C_3$–$C_6$ cycloalkyl; or $R^2$ is a group of the formula:

wherein $R^3$ is $C_1$–$C_6$ alkyl, $C_1$–$C_6$ haloalkyl, phenyl which may be optionally substituted with at least one halogen atom, $C_1$–$C_3$ alkyl group or $C_1$–$C_3$ alkoxy group; or a group of the formula:

wherein $R^4$ and $R^5$ are independently hydrogen, $C_1$–$C_6$ alkyl or $C_1$–$C_6$ haloalkyl; or $R^2$ is a group of the formula:

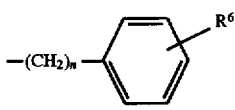

wherein n is an integer of 1 to 5; $R^6$ is hydrogen, halogen, $C_1$–$C_3$ alkyl or $C_1$–$C_3$ alkoxy; or $R^2$ is a group of the formula:

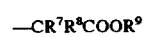

wherein $R^7$ and $R^8$ are independently hydrogen or $C_1$–$C_3$ alkyl; $R^9$ is hydrogen, $C_1$–$C_6$ alkyl, $C_1$–$C_6$ haloalkyl or $C_3$–$C_6$ cycloalkyl; or $R^2$ is a group of the formula:

wherein $R^{10}$ is $C_1$–$C_6$ alkyl or $C_1$–$C_6$ haloalkyl; or phenyl which may be optionally substituted with at least one $C_1$–$C_3$ alkyl group; and —Q is one of the groups Q-7 to Q-8 of the following formulae:

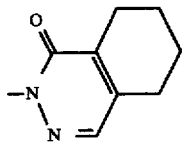  Q-7

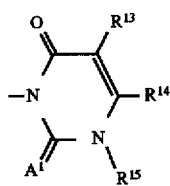  Q-8 wherein $A^1$ is oxygen or sulfur;

$R^{13}$ is hydrogen, halogen or $C_1$–$C_3$ alkyl;

$R^{14}$ is $C_1$–$C_3$ alkyl which may be optionally substituted with at least one halogen atom; and $R^{15}$ is hydrogen, $C_1$–$C_6$ alkyl, $C_3$–$C_6$ alkenyl, $C_3$–$C_6$ alkynyl, amino or benzyl.

2. A compound of the formula:

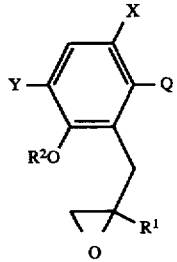  [1]

wherein X is hydrogen, fluorine or chlorine;

Y is fluorine, chlorine or bromine;

$R^1$ is hydrogen or $C_1$–$C_3$ alkyl;

$R^2$ is $C_1$–$C_6$ alkyl, $C_1$–$C_6$ haloalkyl, $C_1$–$C_6$ alkoxy ($C_1$–$C_6$) alkyl, $C_1$–$C_6$ alkoxy ($C_1$–$C_6$) alkoxy ($C_1$–$C_6$) alkyl, $C_1$–$C_6$ alkylthio ($C_1$–$C_6$) alkyl, $C_3$–$C_6$ alkenyl, $C_3$–$C_6$ haloalkenyl, $C_3$–$C_6$ alkynyl, $C_3$–$C_6$ haloalkynyl or $C_3$–$C_6$ cycloalkyl; or $R^2$ is a group of the formula:

wherein $R^3$ is $C_1$–$C_6$ alkyl, $C_1$–$C_6$ haloalkyl, phenyl which may be optionally substituted with at least one halogen atom or $C_1$–$C_3$ alkyl group; or a group of the formula:

wherein $R^4$ and $R^5$ are independently hydrogen, $C_1$–$C_6$ alkyl or $C_1$–$C_6$ haloalkyl; or $R^2$ is a group of the formula:

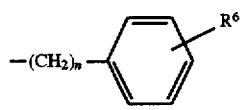

wherein n is an integer of 1 to 5; $R^6$ is hydrogen, halogen or $C_1$–$C_3$ alkyl; or $R^2$ is a group of the formula:

wherein $R^7$ and $R^8$ are independently hydrogen or $C_1$–$C_3$ alkyl; $R^9$ is hydrogen, $C_1$–$C_6$ alkyl, $C_1$–$C_6$ haloalkyl or $C_3$–$C_6$ cycloalkyl; or $R^2$ is a group of the formula:

wherein $R^{10}$ is $C_1$–$C_6$ alkyl or $C_1$–$C_6$ haloalkyl; or phenyl which may be optionally substituted with at least one $C_1$–$C_3$ alkyl group; and —Q is one of the groups Q-7 to Q-8 of the following formulae:

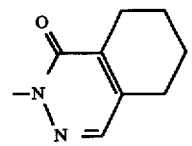  Q-7

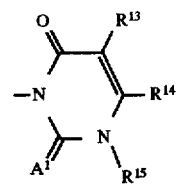  Q-8 wherein $A^1$ is oxygen or sulfur;

$R^{13}$ is hydrogen, halogen or $C_1$–$C_3$ alkyl;

$R^{14}$ is $C_1$–$C_3$ alkyl which may be optionally substituted with at least one halogen atom; and $R^{15}$ is hydrogen, $C_1$–$C_6$ alkyl, $C_3$–$C_6$ alkenyl, $C_3$–$C_6$ alkynyl, amino or benzyl.

3. A compound according to claim 1, wherein —Q is a group of the formula Q-8.

4. A compound according to claim 1, wherein X is hydrogen or fluorine; Y is chlorine; $R^2$ is $C_1$–$C_6$ alkyl, $C_1$–$C_6$ alkoxy ($C_1$–$C_6$) alkyl, $C_1$–$C_6$ alkoxy ($C_1$–$C_6$) alkoxy ($C_1$–$C_6$) alkyl, $C_1$–$C_6$ alkylthio ($C_1$–$C_6$) alkyl, $C_3$–$C_6$ alkenyl or a group of the formula:

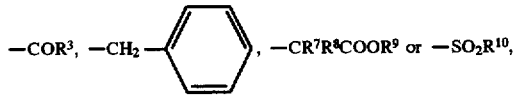

wherein $R^3$ is $C_1$–$C_6$ alkyl, phenyl which may be optionally substituted with at least one $C_1$–$C_3$ alkoxy group; or a group of the formula: —NR$^4$R$^5$, wherein $R^4$ and $R^5$ are independently hydrogen or $C_1$–$C_6$ alkyl; $R^7$ and $R^8$ are independently hydrogen or $C_1$–$C_3$ alkyl; $R^9$ is $C_1$–$C_6$ alkyl; $R^{10}$ is $C_1$–$C_6$ alkyl; —Q is a group of the formula Q-8; $A^1$ is oxygen; $R^{13}$ is hydrogen; $R^{14}$ is $C_1$–$C_3$ alkyl which may be optionally substituted with at least one halogen atom; and $R^{15}$ is $C_1$–$C_6$ alkyl.

5. A compound according to claim 1 wherein $R^1$ is hydrogen or methyl, $R^2$ is acetyl, benzoyl, methylthiomethyl or methoxymethyl.

6. A compound according to claim 1, wherein X is fluorine; Y is chlorine; $R^1$ is methyl; $R^2$ is acetyl or methylthiomethyl; —Q is a group of the formula Q-8; $A^1$ is oxygen; $R^{13}$ is hydrogen; $R^{14}$ is trifluoromethyl; and $R^{15}$ is methyl.

7. A herbicidal composition comprising a herbicidally effective amount of the compound according to claim 1, and an inert career or diluent.

8. A herbicidal composition according to claim 7, wherein the amount of the compound is 0.001% to 90% by weight based on the total weight of the composition.

9. A method for exterminating unfavorable weeds, which comprises applying a herbicidally effective amount of the compound according to claim 1 to an area where the unfavorable weeds grow or will grow.

10. A method according to claim 9, wherein the application amount of the compound is 0.5 to 10,000 g/ha.

11. A compound according to claim 4, wherein $R^1$ is hydrogen or methyl, $R^2$ is acetyl, benzoyl, methylthiomethyl or methoxymethyl.

\* \* \* \* \*